United States Patent
Wyrick

(10) Patent No.: US 7,621,891 B2
(45) Date of Patent: *Nov. 24, 2009

(54) METHOD AND APPARATUS FOR DELIVERING EPINEPHRINE

(75) Inventor: Ronald Wyrick, Spokane, WA (US)

(73) Assignee: Washington Biotech Corporation, Spokane, WA (US)

( * ) Notice: Subject to any disclaimer, the term of this patent is extended or adjusted under 35 U.S.C. 154(b) by 60 days.

This patent is subject to a terminal disclaimer.

(21) Appl. No.: 11/276,460

(22) Filed: Feb. 28, 2006

(65) Prior Publication Data

US 2007/0017532 A1    Jan. 25, 2007

Related U.S. Application Data

(63) Continuation-in-part of application No. 11/175,543, filed on Jul. 6, 2005, now abandoned, which is a continuation-in-part of application No. 11/006,382, filed on Dec. 6, 2004, now Pat. No. 7,297,136.

(51) Int. Cl.
    *A61M 5/00* (2006.01)
(52) U.S. Cl. .............. 604/117; 604/136; 604/139; 604/157; 604/187; 604/197; 604/201; 604/218; 604/232
(58) Field of Classification Search .......... 604/500, 604/511, 68, 71, 117, 136, 138, 181, 187, 604/191, 135, 139, 134, 110, 121, 157, 255, 604/197, 200
    See application file for complete search history.

(56) References Cited

U.S. PATENT DOCUMENTS

| | | | |
|---|---|---|---|
| 4,031,893 A | 6/1977 | Kaplan et al. | |
| 4,578,064 A * | 3/1986 | Sarnoff et al. | ............... 604/191 |
| 4,658,830 A | 4/1987 | Sarnoff | |
| 4,795,433 A | 1/1989 | Sarnoff | |
| 5,078,680 A | 1/1992 | Sarnoff | |
| 5,102,393 A | 4/1992 | Sarnoff et al. | |
| 5,358,489 A * | 10/1994 | Wyrick | ........................ 604/136 |
| 5,540,664 A * | 7/1996 | Wyrick | ........................ 604/136 |
| D375,789 S | 11/1996 | Bryant et al. | |
| 5,578,014 A * | 11/1996 | Erez et al. | .................... 604/192 |
| 5,665,071 A | 9/1997 | Wyrick | |
| 5,695,472 A | 12/1997 | Wyrick | |
| 5,833,669 A | 11/1998 | Wyrick | |
| 6,508,801 B1 | 1/2003 | Fineberg | |
| 6,562,002 B1 | 5/2003 | Taylor et al. | |
| 2003/0004467 A1 | 1/2003 | Musick et al. | |
| 2004/0039336 A1 | 2/2004 | Amark et al. | |

(Continued)

OTHER PUBLICATIONS

Korenblat, et al. "A Retrospective Study of Epinephrine Administration for Anaphylaxis: How Many Doses Are Needed?". Allergy and Asthma 20(6):383-386, 1999.*

(Continued)

*Primary Examiner*—Laura C Schell
(74) *Attorney, Agent, or Firm*—Gregory IPL, P.C.; Randy A. Gregory

(57) ABSTRACT

A method of administering liquid medicine such as epinephrine to a patient includes administering a first dose followed by administering an optional second dose is described herein. Also described herein are devices useful for carrying out the methods described and kits containing these devices.

12 Claims, 18 Drawing Sheets

U.S. PATENT DOCUMENTS

2004/0133159 A1    7/2004    Haider et al.
2006/0129122 A1    6/2006    Wyrick
2007/0017533 A1    1/2007    Wyrick

OTHER PUBLICATIONS

Sampson, Hugh A. "Anaphylaxis and Emergency Treatment". Pediatrics 111: 1601-1608, 2003.*

AAAAI. "Position Statement: Anaphylaxis in Schools and Other Child-Care Settings". <http://www.aaaai.org/media/resources/academy_statements/position_statements/ps34.asp> Jun. 23, 2003: pp. 1-6.*

Korenblat, P. et al., "A Retrospective Study of Epinephrine Administration for Anaphylaxis: How Many Doses Are Needed?", Allergy Asthma Proc. 1999; 20:383-386.

Merck Manual, 17$^{th}$ Ed., 1053-1054 (1999).

Sampson, H.A. et al., "Fatal and Near-Fatal Anaphylactic Reactions to Food in Children and Adolescents," N. Engl. J. Med. 1992;327:380-394.

Sampson, H.A., "Anaphylaxis and Emergency Treatment," Pediatrics 111:1601-1608 (2003).

AAAAI. "Position Statement: Anaphylaxis in Schools and Other Child-Care Settings," http://www.aaaai.org/media/resources/academy_statements/position_statements/ps34.asp Jun. 23, 2003, pp. 1-6.

* cited by examiner

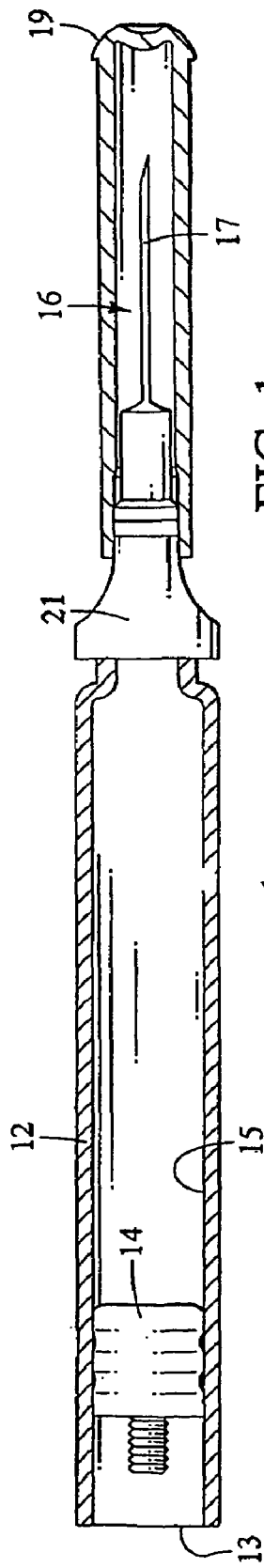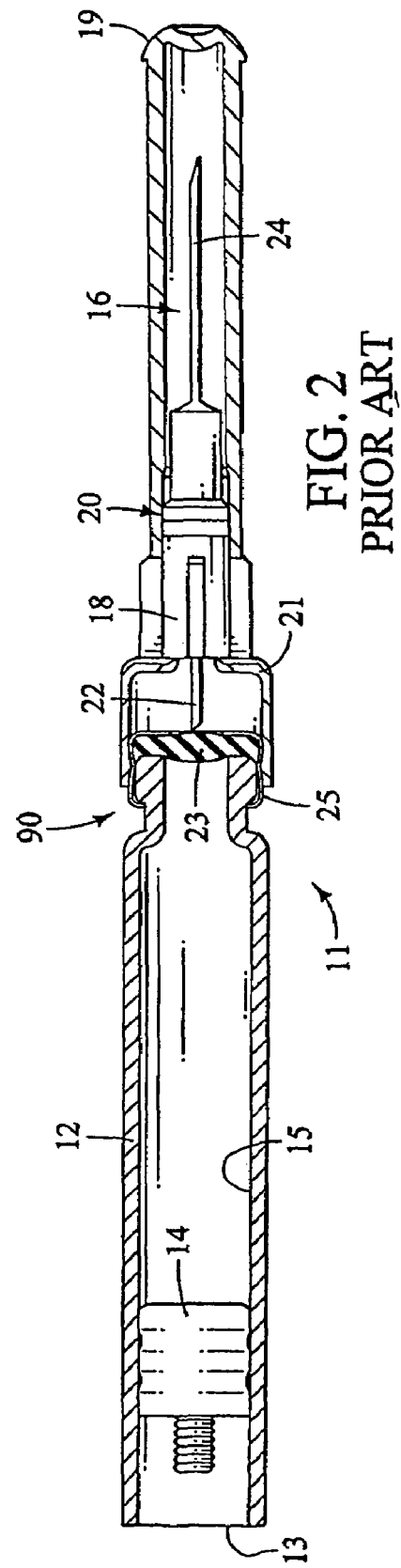

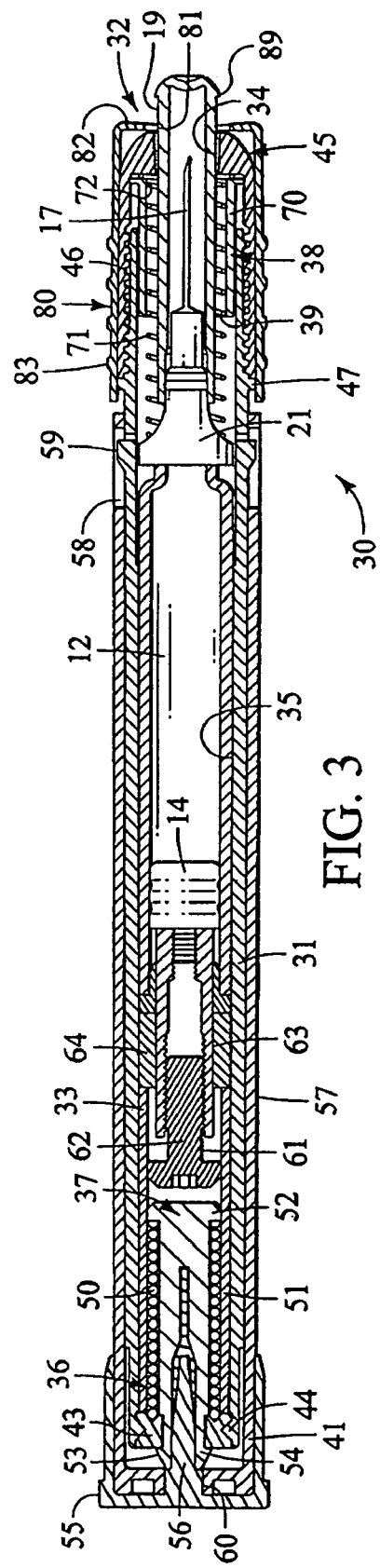
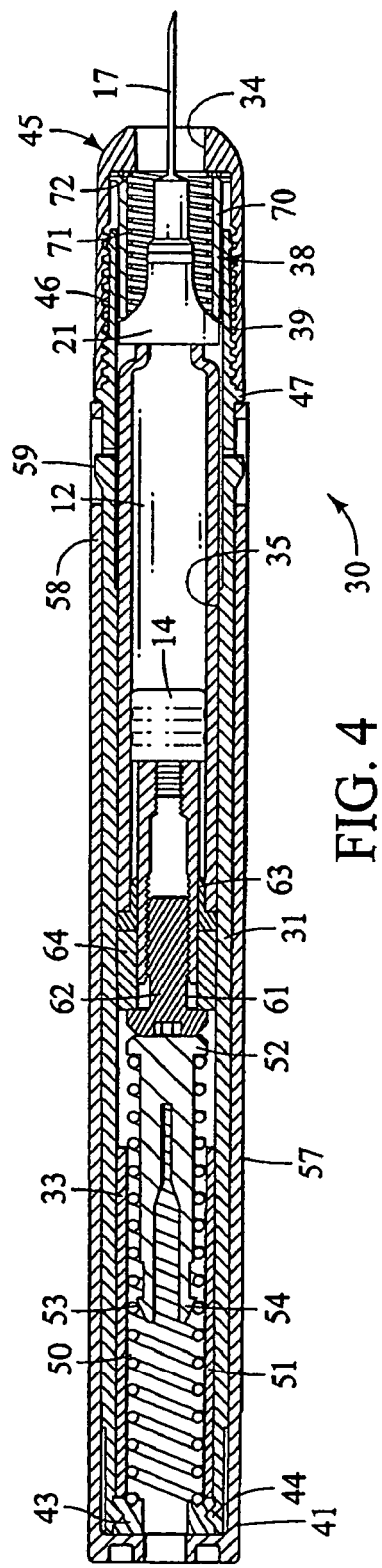
FIG. 3
FIG. 4

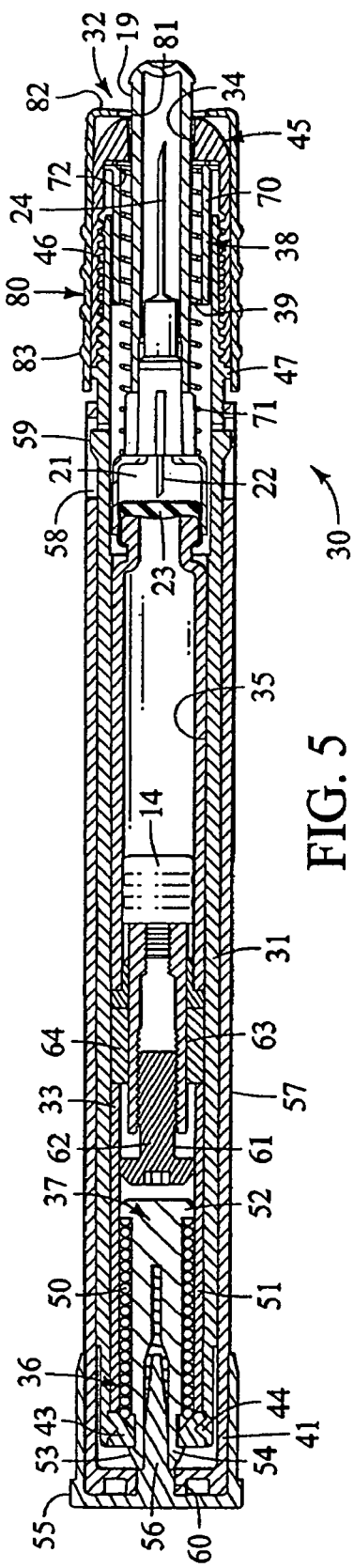
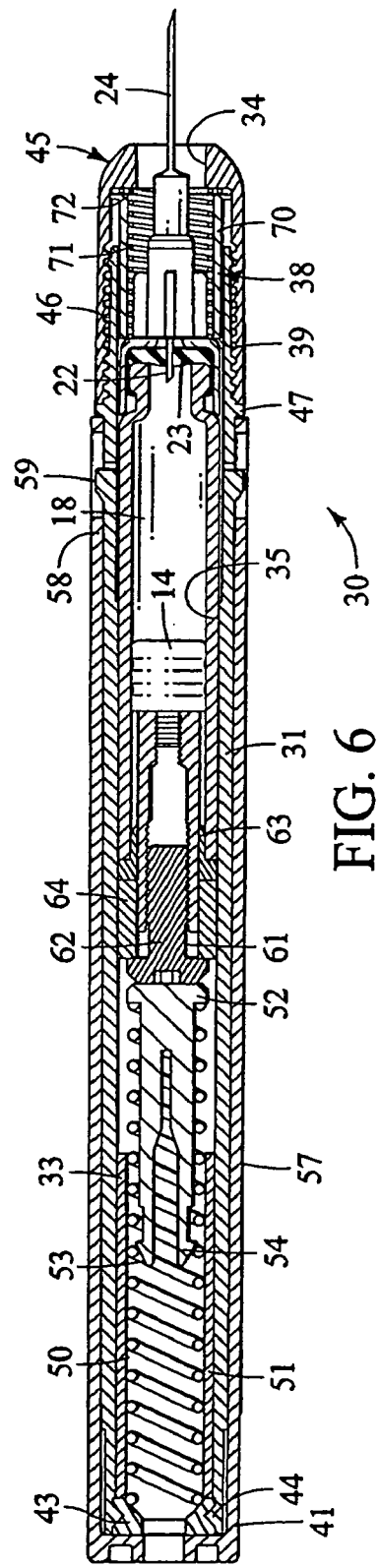

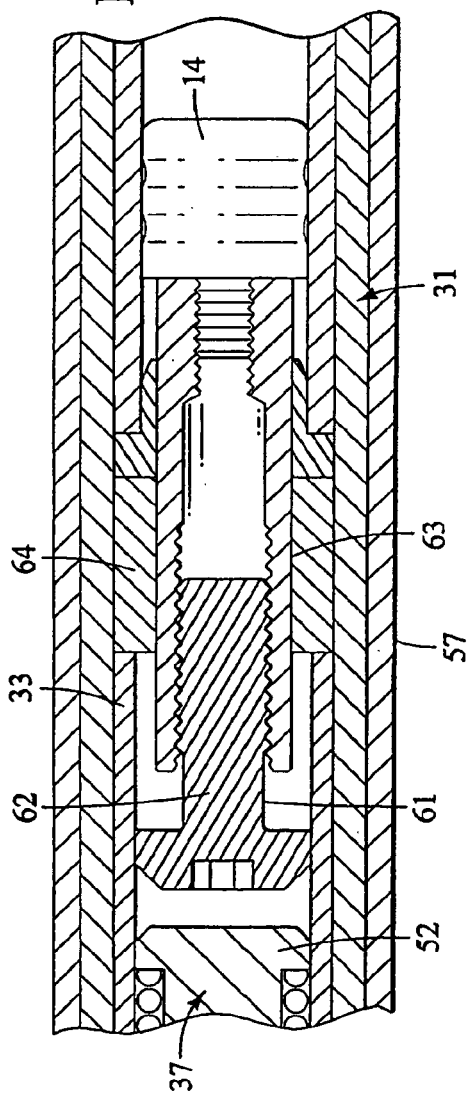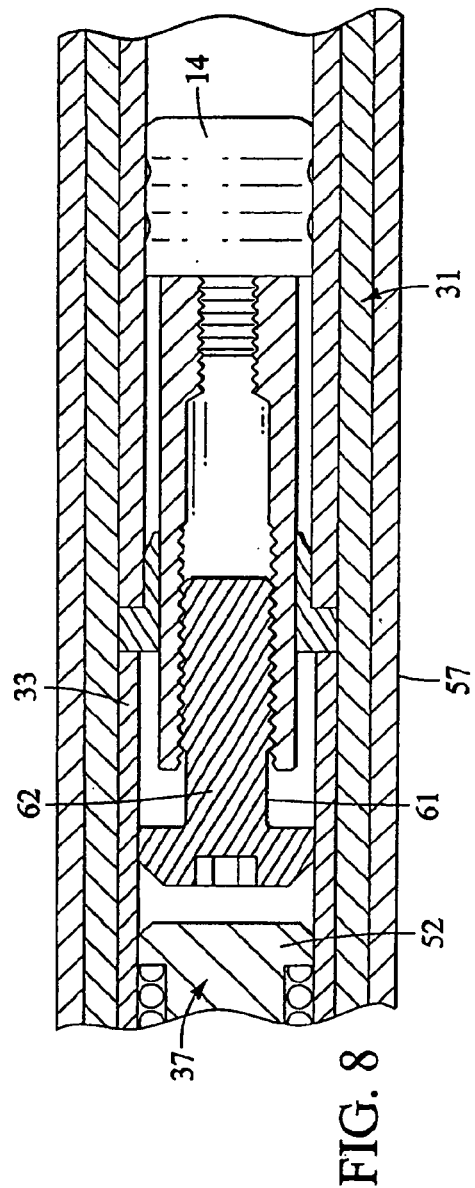

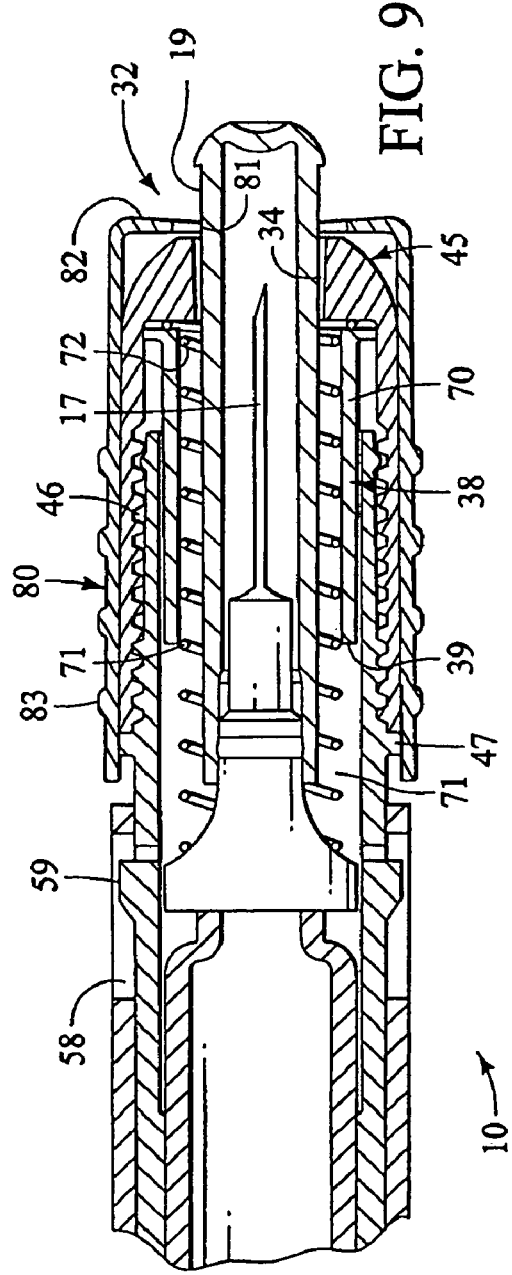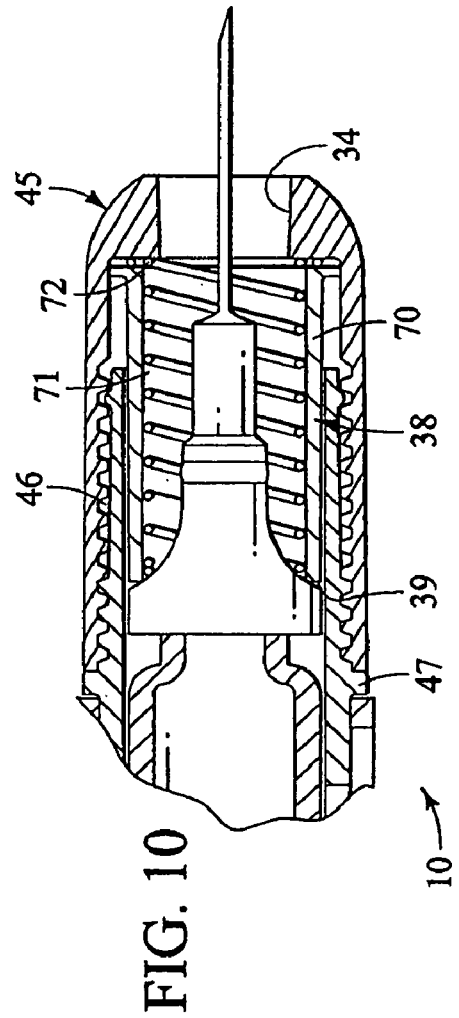

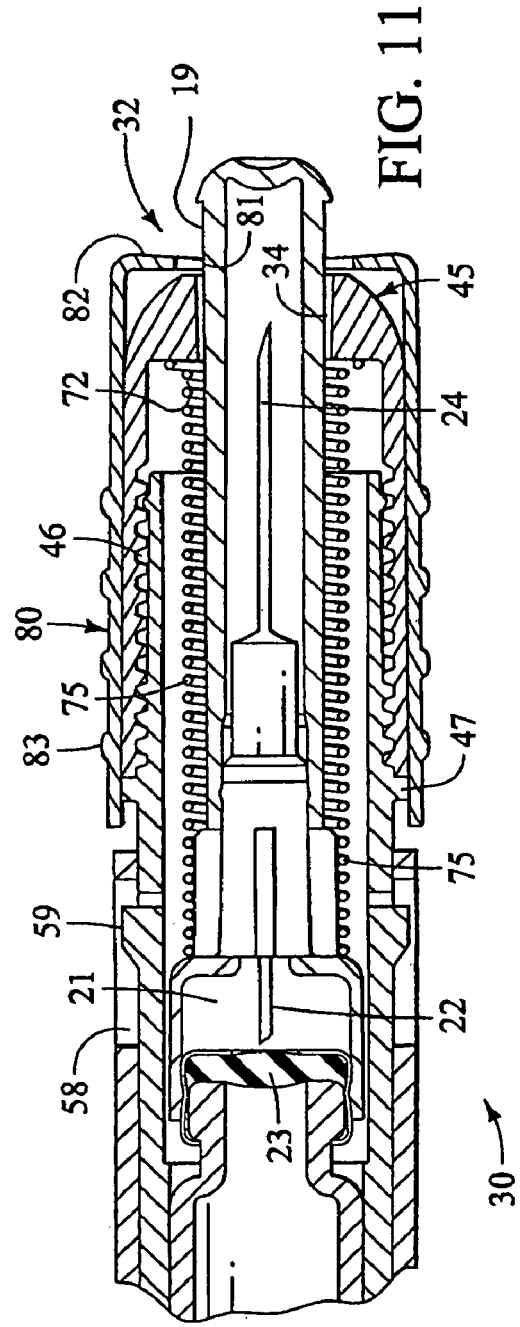
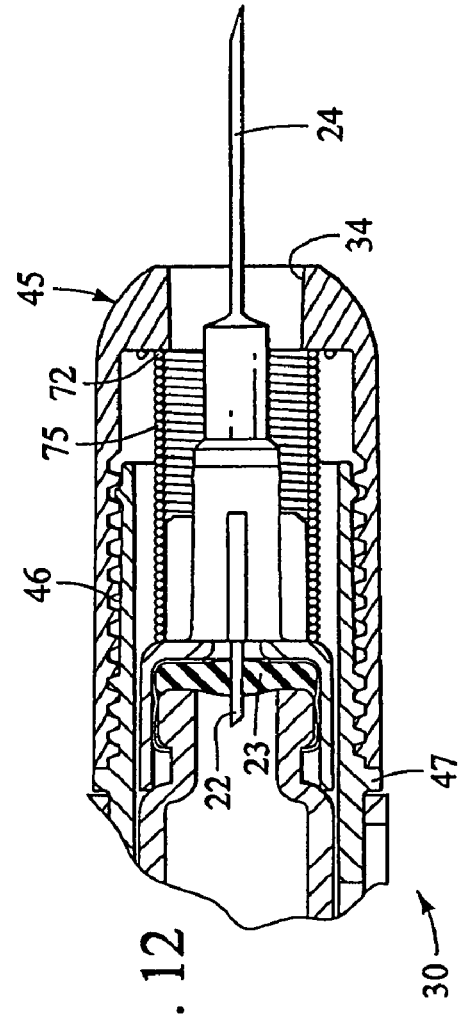
FIG. 11
FIG. 12

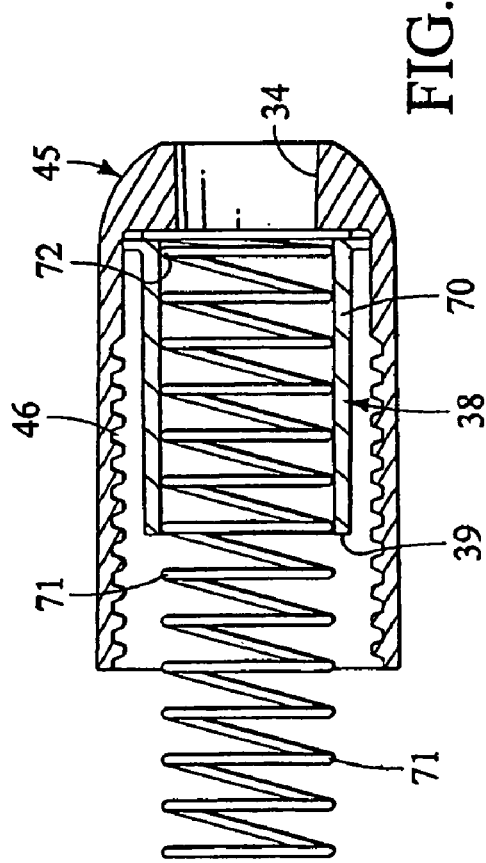
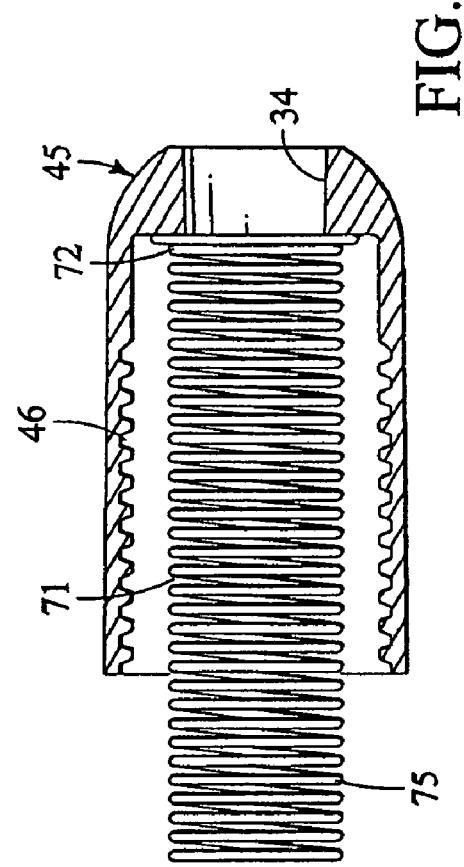
FIG. 13
FIG. 14

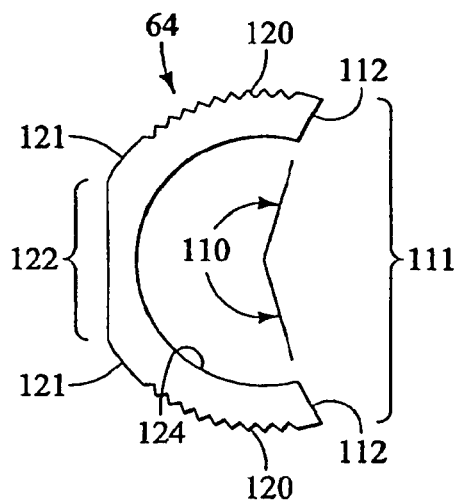 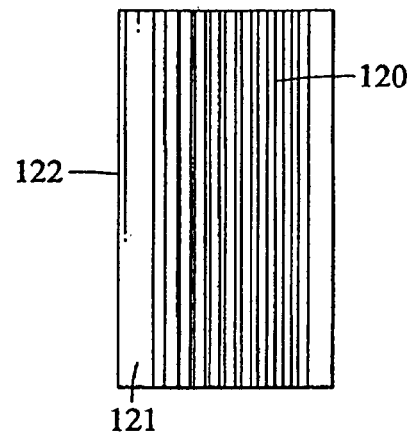
FIG. 16   FIG. 17
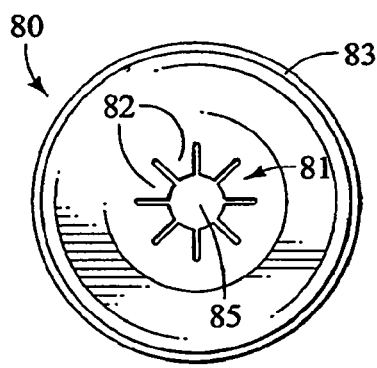 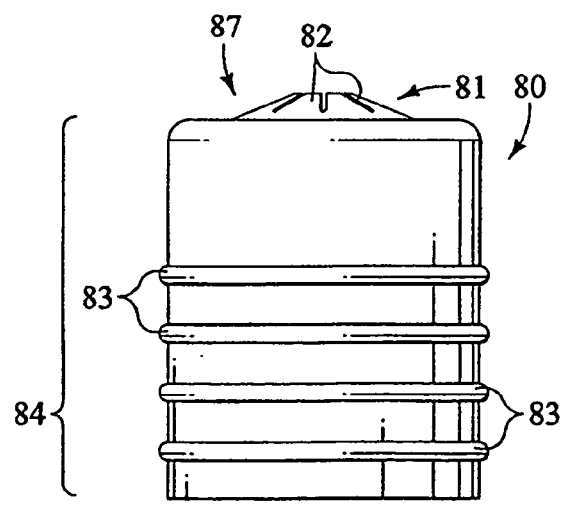
FIG. 18   FIG. 19

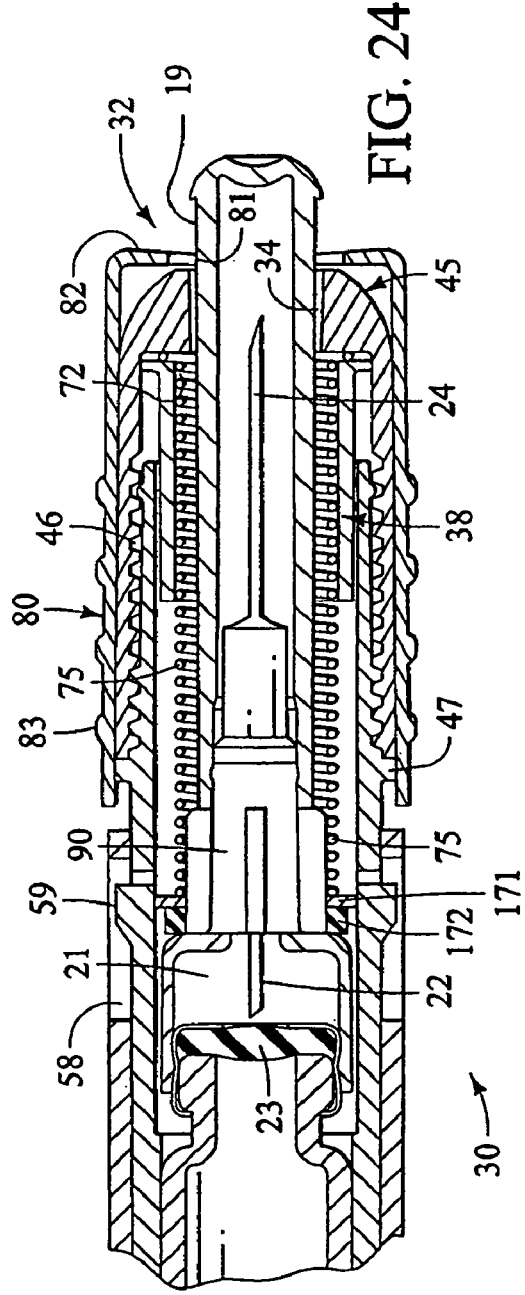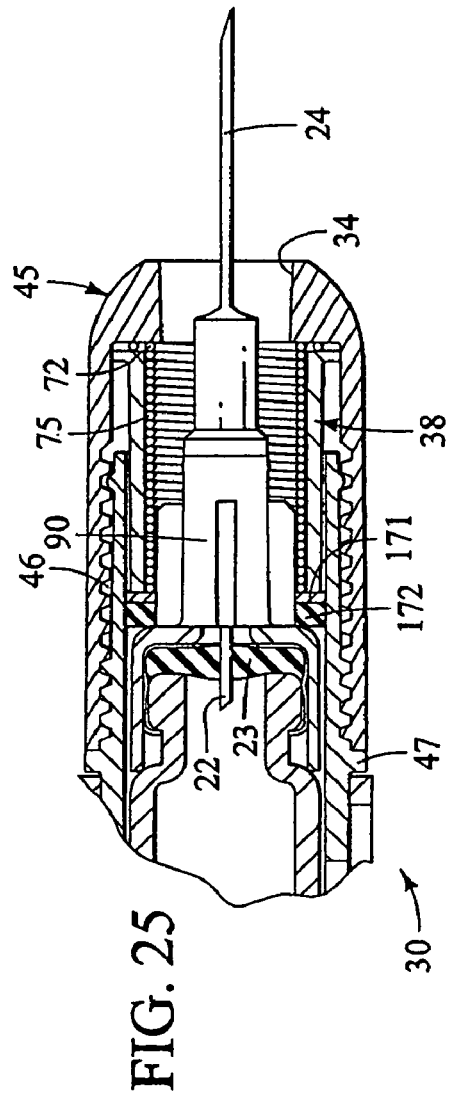

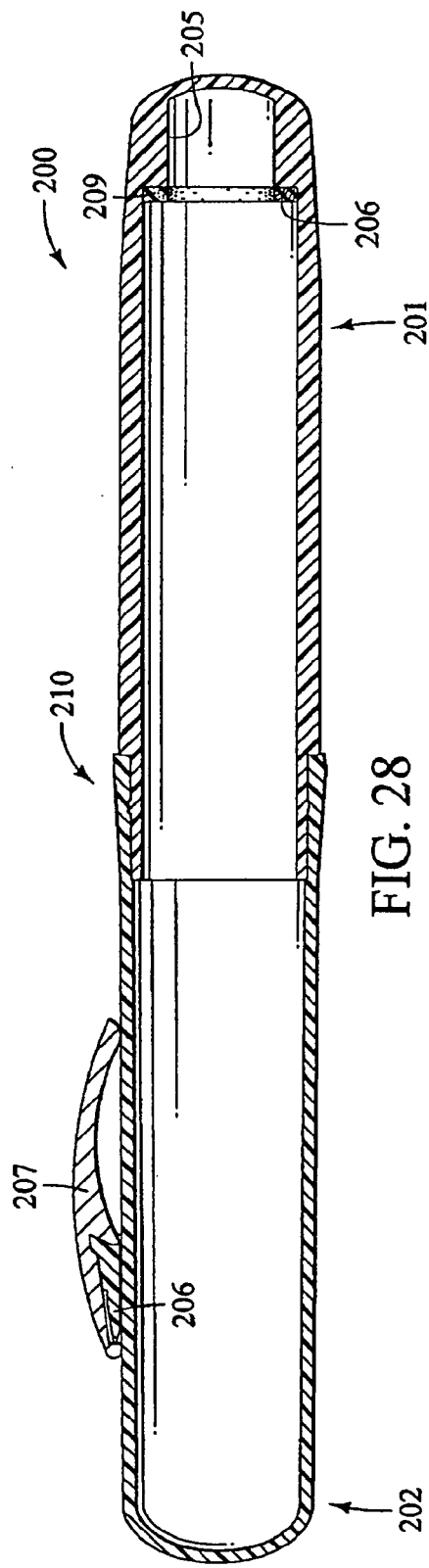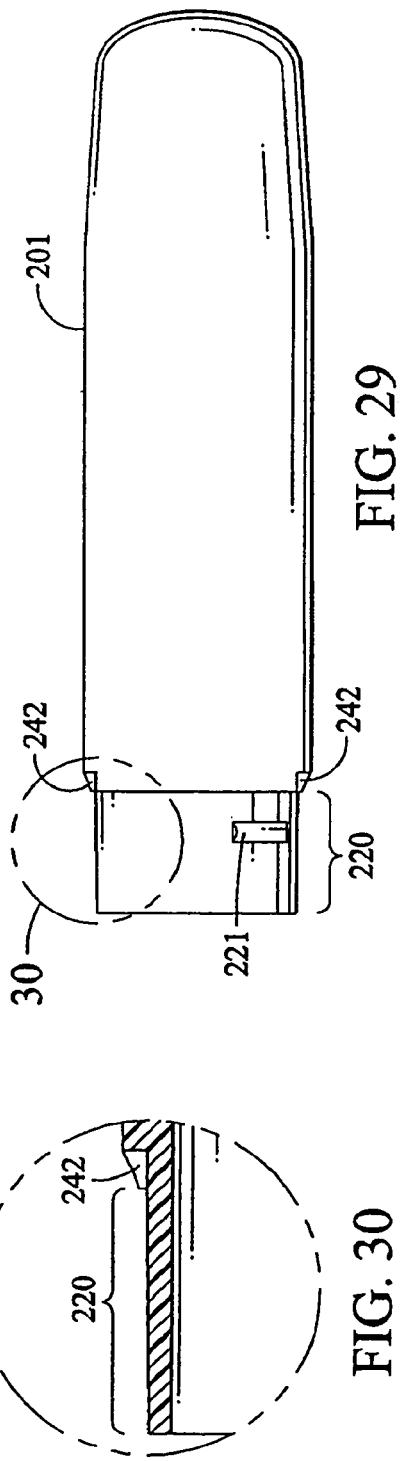
FIG. 28
FIG. 29
FIG. 30

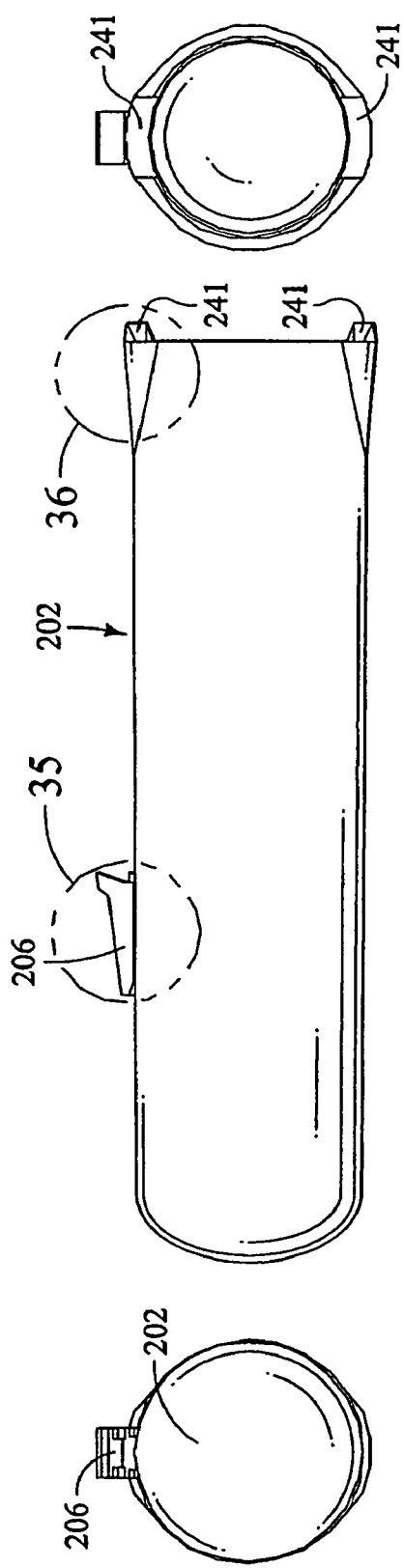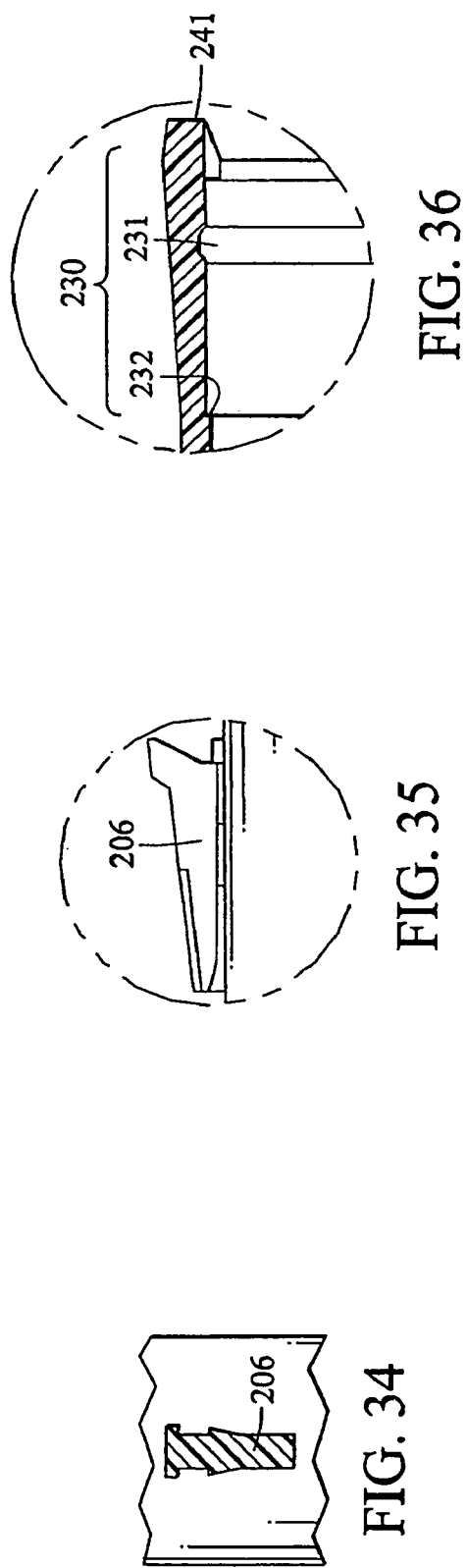

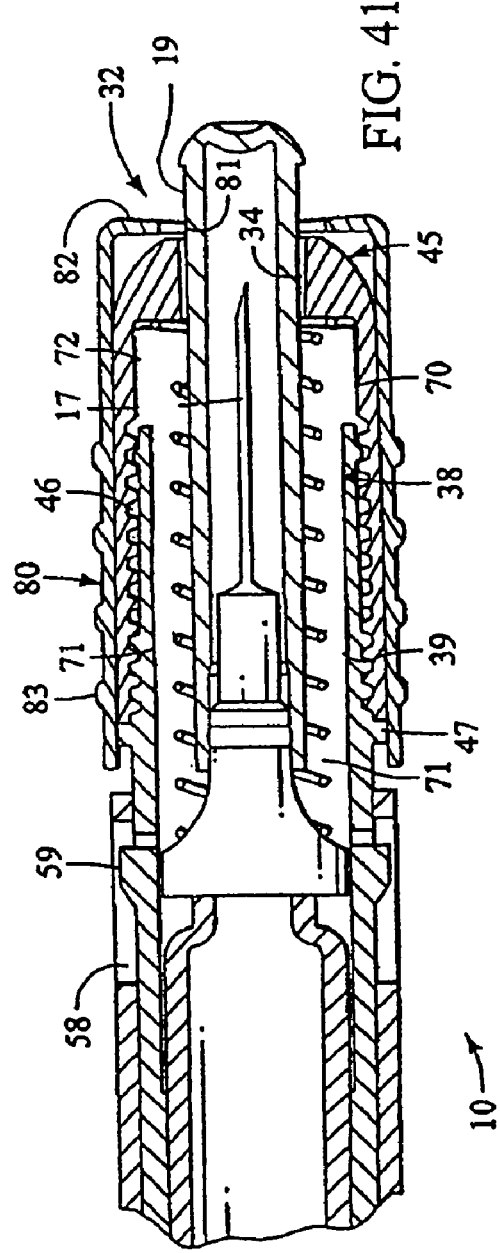
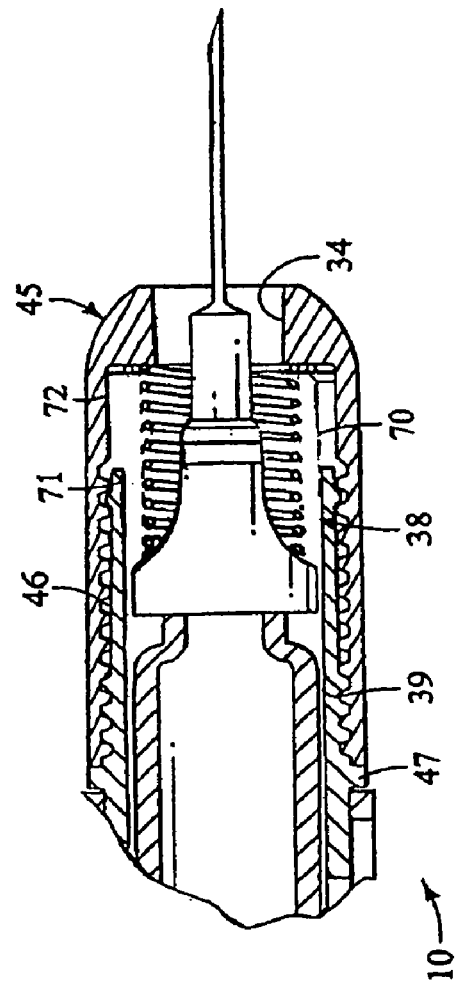
FIG. 41
FIG. 42

METHOD AND APPARATUS FOR DELIVERING EPINEPHRINE

CLAIM FOR PRIORITY

This application is a continuation-in-part application and claims priority to (a) an application filed in the United States with U.S. Ser. No. 11/175,543, filed on Jul. 6, 2005, (b) an application filed in the United States with U.S. Ser. No. 11/006,382, filed on Dec. 6, 2004, and (c) an application filed under PCT Article 8 and PCT Rule 4.10, PCT/US2005/44159, filed in the United States Receiving Office on Dec. 6, 2005, the contents of both of which are incorporated herein by reference in their entirety.

BACKGROUND OF THE INVENTION

Allergic emergencies, such as anaphylaxis, are a growing concern, given the increasing awareness of members of the public of their frequency and potential severity. Anaphylaxis is a sudden, severe, systemic allergic reaction can be fatal, in many cases, if left untreated. Anaphylaxis can involve various areas of the body, such as the skin, respiratory tract, gastrointestinal tract, and cardiovascular system. Acute symptoms occur from within minutes to two hours after contact with the allergy-causing substance; but in rare instances onset may be delayed by as much as four hours. Contact with anaphylaxis-inducing agents, and the severity of the resulting anaphylactic reaction, can be extremely unpredictable. Accordingly, allergists recommend that persons who have a personal or family history of anaphylaxis be prepared to self-administer emergency treatment at all times. Additionally, adults charged with caring for children who are at risk for anaphylaxis should also be prepared to administer anti-anaphylactic first aid.

The symptoms of anaphylaxis include one or more of the following, generally within 1 to about 15 minutes of exposure to the antigen: agitation, a feeling of uneasiness, flushing, palpitations, paresthesias, pruritus, throbbing in the ears, coughing, sneezing, urticaria, angioedema, difficulty breathing due to laryngeal edema or brochospasm, nausea, vomiting, abdominal pain, diarrhea, shock, convulsions, incontinence, unresponsiveness and death. An anaphylactic reaction may include cardiovascular collapse, even in the absence of respiratory symptoms.

According to the Merck Manual, immediate treatment with epinephrine is imperative for the successful treatment of anaphylaxis. Merck Manual, 17$^{th}$ Ed., 1053-1054 (1999). The recommended dose is about 0.01 mL/Kg in adults: usually about 0.3 to 0.5 mL of a 1:1000 dilution of epinephrine in a suitable carrier. While the dose may be given manually, either subcutaneously or intramuscularly, in recent years automatic injectors have become an accepted first aid means of delivering epinephrine. It is recommended that persons at risk of anaphylaxis, and persons responsible for children at risk for anaphylaxis, maintain one or more automatic epinephrine injectors in a convenient place at all times. It is further recommended that, if the symptoms of anaphylaxis persist after the first dose of epinephrine is injected, the patient should be treated with a second dose of epinephrine (about 0.3 mL of the 1:1000 dilution).

Automatic injectors, such as those disclosed in U.S. Pat. Nos. 5,358,489; 5,540,664; 5,665,071 and 5,695,472 (each of which are incorporated herein by reference in its entirety) are known. In general, all automatic injectors contain a volume of epinephrine solution to be injected. In general, automatic injectors include a reservoir for holding the epinephrine solution, which is in fluid communication with a needle for delivering the drug, as well as a mechanism for automatically deploying the needle, inserting the needle into the patient and delivering the dose into the patient. A specific prior art automatic injector is described in U.S. Pat. No. 5,695,472, which is incorporated herein in its entirety.

Automatic injectors for injection of epinephrine solution include automatic injectors covered by U.S. Pat. No. 4,031,893, which is incorporated by reference herein in its entirety. Exemplary injectors provide about 0.3 mL of epinephrine solution at about a concentration of either 0.5 or 1 mg of epinephrine per mL of solution (1:2000 or 1:1000, respectively). Each injector is capable of delivering only one dose of epinephrine and any epinephrine left in the automatic injector (generally about 90% of the original volume of epinephrine) is unavailable for delivery and must be discarded. Thus, if one needs a second dose of epinephrine after the first dose has been delivered, a second automatic injector must be employed. Moreover, if the automatic injector misfires (i.e. fails to deploy the needle, deploys the needle but fails to dispense a dose of epinephrine, etc.), there is no way to access the remaining epinephrine manually. Again, an additional automatic injector unit must be employed in such a situation.

Additionally, the available automatic injectors deliver a uniform volume of 0.3 mL of epinephrine to the patient, whether that patient is an adult or a child. The pediatric version delivers 0.3 mL of a 1:2000 dilution of epinephrine. This volume of medicine can present severe discomfort to smaller children, which can lead to poor patient compliance or non-compliance. Given the acute and potentially lethal threat presented by anaphylaxis, prompt and diligent patient compliance is a must.

Thus, there is a need for a method of treating anaphylaxis, wherein two doses of epinephrine may be delivered from the same device. There is further a need for a device adapted to deliver two doses of epinephrine to the same patient. There is also a need for a method of treating anaphylaxis in a person of less than about 15 Kg, wherein a smaller volume of epinephrine can be delivered to the patient. There is also a need for a device capable to delivering two such smaller doses to a patient of less than about 15 Kg.

The invention meets the foregoing needs and provides related advantages as well.

SUMMARY OF THE INVENTION

The present invention meets the foregoing and related needs by providing an improved method of treating allergic emergencies, such as anaphylaxis, with epinephrine. The method comprises injecting into a patient a first dose of epinephrine and later injecting, from the same device, a second dose of epinephrine. The essential feature of one preferred embodiment of the invention is administration of a first dose of an epinephrine solution containing about 0.15 mg of epinephrine, optionally followed by a second dose of an epinephrine solution containing about 0.15 mg of epinephrine, wherein the total amount of epinephrine delivered between the first and second doses is 0.3 mg. The essential feature of the second preferred embodiment of the invention is administration of a first dose of an epinephrine solution containing about 0.30 mg of epinephrine, optionally followed by a second dose of an epinephrine solution containing about 0.30 mg of epinephrine, wherein the total amount of epinephrine delivered between the first and second doses is 0.6 mg. The first dose may be delivered by either an automatic injection or a manual injection, and the second dose may be delivered by either an automatic injection or a manual injection. In some embodiments of the invention, both the first dose and second dose are delivered by automatic injection from the same device. In other embodiments, both the first dose and the second dose are delivered by manual injection from the same device, and in other embodiments, one dose is administered by manual injection and the other dose by automatic injection from the same device, and in particular, the first dose is delivered by manual injection and the second dose is delivered by automatic injection from the same device.

The invention further provides another improved method of treating medical emergencies, such as anaphylaxis, with epinephrine. The method comprises injecting into a patient a first dose of epinephrine and later injecting, from the same device, a second dose of epinephrine. The first dose is delivered by either an automatic injection or a manual injection, and the second dose is delivered by either an automatic injection or a manual injection. In some embodiments of the invention, both the first dose and second dose are delivered by automatic injection from the same device. In other embodiments, both the first dose and the second dose are delivered by manual injection from the same device, and in other embodiments, one dose is administered by manual injection and the other dose by automatic injection, and in particular, the first dose is delivered by manual injection and the second dose is delivered by automatic injection from the same device.

Thus, methods of treating allergic emergency in a patient, comprising injecting into a patient in need thereof a first dose of epinephrine comprising about 0.3 mL of an epinephrine solution and optionally subsequently administering a second dose of epinephrine comprising about 0.3 mL or about 0.15 mL of the epinephrine solution are provided herein. In some embodiments, the first dose of epinephrine comprises about 0.3 mL of the epinephrine solution and the second dose of epinephrine comprises about 0.3 mL of the epinephrine solution. In other embodiments, the first dose of epinephrine comprises about 0.15 mL of the epinephrine solution and the second dose of epinephrine comprises about 0.15 mL of the epinephrine solution. The essential features of the preferred embodiments of the invention are administration of a first dose of an epinephrine solution, optionally followed by a second dose of an epinephrine solution, wherein the total amount of epinephrine delivered between the first and second doses is either 0.3 mg or 0.6 mg. Specific preferred methods are provided below.

Methods of treating allergic emergency in a patient, comprising automatically injecting into a patient in need thereof a first dose of epinephrine comprising about 0.3 mL of an epinephrine solution and optionally subsequently automatically injecting into the patient a second dose of epinephrine comprising about 0.3 mL the epinephrine solution, wherein the total amount of epinephrine delivered between the first and second doses is either 0.3 mg or 0.6 mg, are provided herein.

Methods of treating allergic emergency in a patient, comprising manually injecting into a patient in need thereof a first dose of epinephrine comprising about 0.3 mL of an epinephrine solution and optionally subsequently manually injecting into the patient a second dose of epinephrine comprising about 0.3 mL the epinephrine solution, wherein the total amount of epinephrine delivered between the first and second doses is either 0.3 mg or 0.6 mg, are also provided herein.

Methods of treating allergic emergency in a patient, comprising manually injecting into a patient in need thereof a first dose of epinephrine comprising about 0.15 mL of an epinephrine solution and optionally subsequently manually injecting into the patient a second dose of epinephrine comprising about 0.15 mL the epinephrine solution, wherein the total amount of epinephrine delivered between the first and second doses is either 0.3 mg or 0.6 mg, are provided herein.

Methods of treating allergic emergency in a patient, comprising automatically injecting into a patient in need thereof a first dose of epinephrine comprising about 0.15 mL of an epinephrine solution and optionally subsequently automatically injecting into the patient a second dose of epinephrine comprising about 0.15 mL the epinephrine solution, wherein the total amount of epinephrine delivered between the first and second doses is either 0.3 mg or 0.6 mg, are also provided herein.

Although the essential feature of one preferred embodiment of the invention is administration of a first dose of an epinephrine solution containing about 0.15 mg of epinephrine, optionally followed by a second dose of an epinephrine solution containing about 0.15 mg of epinephrine, wherein the total amount of epinephrine delivered between the first and second doses is 0.3 mg, and the essential feature of another preferred embodiment of the invention is administration of a first dose of an epinephrine solution containing about 0.30 mg of epinephrine, optionally followed by a second dose of an epinephrine solution containing about 0.30 mg of epinephrine, wherein the total amount of epinephrine delivered between the first and second doses is 0.6 mg, in some embodiments, to obtain these weight amounts of epinephrine, the concentration of the first dose of epinephrine solution is selected from about 0.5 mg epinephrine per mL of epinephrine solution, about 1.0 mg of epinephrine per mL of epinephrine solution, about 1.5 mg of epinephrine per mL of epinephrine solution, and about 2.0 mg of epinephrine per mL of epinephrine solution. In other embodiments, the concentration of the second dose of epinephrine solution is selected from about 0.5 mg epinephrine per mL of epinephrine solution, about 1.0 mg of epinephrine per mL of epinephrine solution, about 1.5 mg of epinephrine per mL of epinephrine solution, and about 2.0 mg of epinephrine per mL of epinephrine solution. In various embodiments, the concentration of the first dose of the epinephrine solution is different from the concentration of the second dose of the epinephrine solution. Alternatively, the concentration of the first dose of the epinephrine solution is about the same as the concentration of the second dose of the epinephrine solution. In preferred embodiments, the concentration of the first dose is about 0.5 mg epinephrine per mL of epinephrine solution or about 1.0 mg of epinephrine per mL of epinephrine solution and the concentration of the second dose is about 0.5 mg epinephrine per mL of epinephrine solution or about 1.0 mg of epinephrine per mL of epinephrine solution.

In various embodiments of the methods described herein, the first and second doses are injected subcutaneously, or the first does is injected subcutaneously and the second dose is injected intramuscularly, or the first dose is injected intramuscularly and the second dose is injected subcutaneously, or the first and second doses are each injected intramuscularly.

In some embodiments of the methods described herein, the second dose is injected less than about 30 minutes after the first dose, or less than 20 minutes after the first dose, or less than about 10 minutes after the first dose.

In some embodiments, the patient weighs about 30 Kg or less than about 15 Kg. In some embodiments, the patient is an adult. In other embodiments, the patient is a child of age 12 or older.

In some embodiments, both the first and second doses are self-administered by the patient. Alternatively, the first dose can be self-administered by the patient and the second dose is administered by someone other than the patient, or the first dose can be administered by someone other than the patient and the second dose can be administered by the patient, or both the first and second doses are administered by someone other than the patient.

The invention further provides improved devices for treating allergic emergencies, such as anaphylaxis. The device contains means for delivering a first dose of about 0.15 mL or about 0.3 mL of and epinephrine solution to a patient as well as means for delivering a second dose of about 0.15 mL or about 0.3 mL of the epinephrine solution, wherein the total amount of epinephrine delivered between the first and second doses is either 0.3 mg or 0.6 mg, to a patient. In some embodiments of the invention, the device is constructed so as to deliver both the first dose and second dose by automatic injections. In other embodiments, the device is constructed to deliver both the first and second dose by manual injections, and in other embodiments, the device is constructed so that one dose is delivered by manual injection and one dose by automatic injection, and in particular, the device is constructed so that the first dose is delivered by manual injection and the second dose is delivered by automatic injection from the same device.

Drug delivery devices containing an epinephrine solution are provided herein, wherein the device comprises means for delivering a first dose of about 0.15 mL of the epinephrine solution by automatic injection and means for delivering a second dose of about 0.15 mL of the epinephrine solution, wherein the total amount of epinephrine delivered between the first and second doses is either 0.3 mg or 0.6 mg, by automatic injection.

Dug delivery devices containing an epinephrine solution are provided herein, wherein the device comprises means for delivering a first dose of about 0.3 mL of the epinephrine solution by manual injection and means for delivering a second dose of about 0.3 mL of the epinephrine solution, wherein the total amount of epinephrine delivered between the first and second doses is either 0.3 mg or 0.6 mg, by manual injection.

Drug delivery devices containing an epinephrine solution are provided herein, wherein the device comprises means for delivering a first dose of about 0.15 mL of the epinephrine solution by manual injection and means for delivering a second dose of about 0.15 mL of the epinephrine solution, wherein the total amount of epinephrine delivered between the first and second doses is either 0.3 mg or 0.6 mg, by manual injection.

Drug delivery devices containing an epinephrine solution are provided herein, wherein the device comprises means for delivering a first dose of about 0.3 mL of the epinephrine solution by automatic injection and means for delivering a second dose of about 0.3 mL of the epinephrine solution, wherein the total amount of epinephrine delivered between the first and second doses is either 0.3 mg or 0.6 mg, by automatic injection.

Also provided herein are kits for treatment of anaphylaxis comprising the drug delivery devices described herein and instructions for administration. In some embodiments, the kit further comprises means for holding the drug delivery device and the instructions.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Certain embodiments of the invention are described below with reference to the following accompanying drawings.

FIG. 1 is a side sectional view of a hypodermic syringe subassembly of the single needle variety. This is also a view of one embodiment of a syringe according to the present invention after it has been removed from an automatic injector as described herein.

FIG. 2 is a side sectional view of a double needle syringe subassembly. This is also a view of one embodiment of a syringe according to the present invention after it has been removed from an automatic injector as described herein.

FIG. 3 is a side sectional view of a first embodiment of an automatic injector device according to the invention in a cocked condition.

FIG. 4 is a side sectional view similar to FIG. 3 showing the needle in an extended condition.

FIG. 5 is a side sectional view similar to FIG. 3 in which a double needle syringe subassembly is in a cocked condition.

FIG. 6 is a side sectional view similar to FIG. 5 showing the double needle syringe assembly in an extended condition.

FIG. 7 is an enlarged sectional detail view of a dosage adjustment and stop arrangement by which multiple (i.e., two) dosages may be administered from the same syringe subassembly.

FIG. 8 is a view similar to the detail view of FIG. 7 showing a stop collar removed and the remaining components of FIG. 7 in position for a second dose.

FIG. 9 is an enlarged sectional detail view of a sleeve penetration controller 38 embodiment used in conjunction with a single needle subassembly, with the needle in a retracted position.

FIG. 10 is a view similar to FIG. 9 showing the syringe subassembly engaging the sleeve penetration controller 38 and the needle extended to a desired penetration depth.

FIG. 11 is an enlarged sectional detail view of a compression spring penetration controller 38 used in conjunction with a double needle subassembly, with the needle in a retracted position.

FIG. 12 is a view similar to FIG. 11 only showing the ampule 12 seal pierced, the compression spring penetration controller 38 compressed, and the forward needle in an extended position.

FIG. 13 is a sectional view showing an end cap and penetration controller 38 in which any of various length control sleeves can be selected and installed for variably controlling needle penetration to various selected penetration depths.

FIG. 14 is a sectional view showing the end cap and one compression spring penetration controller 38 installed. Various lengths and other parameters of control springs may be used for controlling needle penetration to various selected depths.

FIG. 16 is a top view of a preferred stop collar.

FIG. 17 is a side elevation view of the stop collar of FIG. 16.

FIG. 18 is an end view of a preferred sheath remover 80.

FIG. 19 is a side view of the sheath remover 80 of FIG. 18.

FIG. 24 is an enlarged partial side sectional view of a muzzle end of a preferred injector construction having a resilient pad and load distribution and guide ring positioned between the syringe shoulder. The injector is in a cocked condition with the syringe retracted.

FIG. 25 is a view similar to FIG. 24 with the injector shown with the syringe assembly in an extended position.

FIG. 28 is a sectional view showing a preferred auto-injector storage case according to the inventions, FIG. 29 is a side view of a bottom part of the case shown in FIG. 28.

FIG. 30 is an enlarged detail sectional view as shown in circle 30 of FIG. 29.

FIG. 31 is a side view of an upper part of the case shown in FIG. 28.

FIG. 32 is a top end view of the upper case part shown in FIG. 31.

FIG. 33 is a bottom end view of the upper case part shown in FIG. 31.

FIG. 34 is a detail view showing a mounting extension forming part of the upper case part of FIG. 31.

FIG. 35 is a side detail view of the mounting extension used to mount a clip to the upper case pat of FIG. 31, taken at circle 35 of FIG. 31.

FIG. 36 is an enlarged sectional view taken at circle 36 of FIG. 31.

FIG. 41 is an enlarged sectional detail view of the nose cap subassembly in one embodiment of the invention, similar to FIG. 9, except without installation of penetration controller 38, with the needle in a retracted position.

FIG. 42 is a view similar to FIG. 41 showing the needle in one embodiment of the invention extended to a desired penetration depth, and is similar to FIG. 10, except without installation of penetration controller 38.

DETAILED DESCRIPTION OF THE INVENTION

Figure 15A:
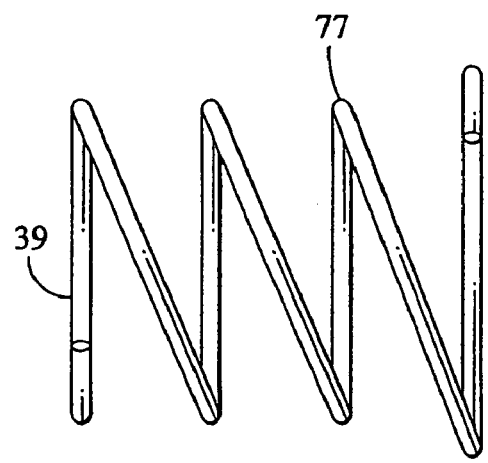
FIGS. 15A-15F are side views showing different compression spring penetration controller 38s of various lengths and helical advance rates that affect needle penetration depth.

The present invention provides methods for treating allergic emergencies, such as anaphylaxis. The invention further provides devices for treating allergic emergencies, such as anaphylaxis. Furthermore the invention provides kits for treating allergic emergencies, such as anaphylaxis. As described above, anaphylaxis means an acute and severe allergic reaction to an allergen (antigen). Treatment of anaphylaxis means ameliorating or alleviating the symptoms of anaphylaxis. Such treatment may be, and in most cases is, temporary. For example, in embodiments of the invention the method, device or kit of the invention will provide emergency relief from the symptoms of anaphylaxis for a time sufficient for the patient to seek professional medical assistance. Thus, devices and kits of the invention are well suited for inclusion in first aid kits in professional child care settings and homes, especially where one or more persons at risk for anaphylaxis are known to dwell. They are also well suited for inclusion in so-called crash carts in medical emergency rooms. They may also be conveniently carried by those who are at risk for anaphylaxis or those who are charged with caring for those who are at risk for anaphylaxis. The methods of the invention are suitable for treating persons who are at risk for allergic emergencies, such as anaphylaxis, in any of the aforementioned settings.

Thus, treatment of an allergic emergency includes treatment of anaphylaxis, for which the invention is especially well-suited. In addition, treatment of allergic emergency includes treatment of other allergic conditions that may be treated with epinephrine. For example, the symptoms of anaphylactoid reactions to drugs closely mimic those of anaphylaxis and are treated in a similar manner. In cases where it is not clear whether the reaction is a systemic immunological response (anaphylaxis) or a systemic toxic response (anaphylactoid reaction), the accepted first line of treatment is with epinephrine. In this sense, treatment of an allergic emergency encompasses treatment of anaphylaxis, an anaphylactoid response or both.

In some embodiments, the present invention provides a method of treating an allergic emergency, such as anaphylaxis, in a patient, comprising administering to the patient two doses of epinephrine from the same device. The method includes injecting into a patient in need thereof a first dose of epinephrine comprising about 0.3 mL of an epinephrine solution and subsequently injecting into the patient a second dose of epinephrine comprising about 0.3 mL the epinephrine solution, wherein the total amount of epinephrine delivered between the first and second doses is either 0.3 mg or 0.6 mg. In some of these embodiments, the method includes automatically injecting both the first and the second doses with an injection device. In other embodiments, the method includes manually injecting both the first and the second doses with an injection device. In yet other embodiments, the method includes injecting one of the doses automatically, and one of the doses manually, with an injection device, and in particular, the first dose is delivered by manual injection and the second dose is delivered by automatic injection from the same device. The concentration of epinephrine in the epinephrine solution can be, for example, about 0.5 mg of epinephrine per mL of solution, or about 1 mg of epinephrine per mL of solution, or about 1.5 mg of epinephrine per mL of solution, or about 2.0 mg of epinephrine per mL of solution. In any event, the total amount of epinephrine delivered between the first and second doses is either 0.3 mg or 0.6 mg. With the teachings provided herein, one of skill in the art will understand that to decrease the volume of solution administered, but achieve the same dose, the concentration of the solution must be increased. Likewise, to decrease the amount of epinephrine delivered in a dose with an equivalent volume, the concentration of the solution should be decreased. Thus, where a specific volume is described, it is contemplated that varying amounts of epinephrine can be administered by varying the concentration of the epinephrine solutions. Moreover, where a specific amount of epinephrine is described, it is also contemplated by the current invention that that amount of epinephrine can be administered in different volumes of solution.

In some embodiments, in addition to epinephrine, the solution also contains one or more inactive ingredients, such as sodium bisulfite as a preservative, a pH buffer, an ingredient that provides isotonicity, or mixtures thereof. The first dose may be self-administered by the patient, or may be administered by someone other than a patient, such as a caretaker or a medical professional.

It is necessary that the patient monitor his or her symptoms, or that the person caring for the patient monitors the patient's symptoms directly. In cases where the symptoms of anaphylaxis are not suitably ameliorated by administration of the first injection of 0.3 mg epinephrine in solution (whether by manual or automatic injection), it will be necessary to administer a second dose. The concentration of epinephrine solution can be, for example, about 0.5 mg of epinephrine per mL of solution, or about 1 mg of epinephrine per mL of solution, or about 1.5 mg of epinephrine per mL of solution, or about 2.0 mg of epinephrine per mL of solution, wherein the total amount of epinephrine delivered between the first and second doses is either 0.3 mg or 0.6 mg. In some embodiments, when the concentration is higher or lower than 1 mg of epinephrine per mL of solution, the volume is adjusted accordingly.

Additionally, in cases where the patient is unable to obtain professional medical assistance before the beneficial effects of the first dose begin to subside, it will be necessary to administer a second dose (whether by manual or automatic injection). Thus, in certain embodiments, the second dose is administered less than about 30 minutes after the first dose, e.g. less than about 20 minutes after the first dose. In particular embodiments, the second dose is administered less than about 10 minutes after the first dose. In some of these embodiments, the method includes automatically injecting both the first and the second doses with an injection device. In other embodiments, the method includes manually injecting both the first and the second doses with an injection device. In yet other embodiments, the method includes injecting one of the doses automatically, and one of the doses manually, with an injection device, and in particular, injecting the first dose manually and the second dose automatically.

The second dose may be self-administered by the patient or administered by someone other than the patient. In some embodiments, both the first and second dose are self-administered by the patient, both the first and second doses are administered by a person other than the patient, the first dose is self-administered and the second is administered by someone other than the patient or the first dose is administered by someone other than the patient and the second dose is self-administered by the patient.

A first, automatically or manually injected dose of 0.3 mL epinephrine solution followed by a second, automatically or manually injected dose of the same epinephrine solution is considered especially suitable for treating adults and children of over 15 Kg body weight. Thus, in some embodiments, the weight of the patient weighs at least about 30 Kg. In other embodiments, the patient weighs at least about 15 Kg. The 0.3 mL dose is also especially suitable for treating adults and children of 12 years of age and older. The concentration of epinephrine solution can be, for example, about 0.5 mg of epinephrine per mL of solution, or about 1 mg of epinephrine per mL of solution, or about 1.5 mg of epinephrine per mL of solution, or about 2.0 mg of epinephrine per mL of solution, wherein the total amount of epinephrine delivered between the first and second doses is either 0.3 mg or 0.6 mg. In some embodiments, when the concentration is higher or lower than 1 mg of epinephrine per mL of solution, the volume is adjusted accordingly.

A first, automatically or manually injected dose of 0.3 mL (i.e., 0.3 mg epinephrine in a 1 mg/mL solution) followed by a second, automatically or manually injected dose of the same epinephrine solution is considered especially suitable for treating adults and children of over 12 years of age and older. Thus, in some embodiments, the patient is an adult. In other embodiments, the patient is a child of 12 years of age or older. The concentration of epinephrine solution can be, for example, about 0.5 mg of epinephrine per mL of solution, or about 1 mg of epinephrine per mL of solution, or about 1.5 mg of epinephrine per mL of solution, or about 2.0 mg of epinephrine per mL of solution, wherein the total amount of epinephrine delivered between the first and second doses is 0.6 mg. In some embodiments, when the concentration is higher or lower than 1 mg of epinephrine per mL of solution, the volume is adjusted accordingly.

In some embodiments, the present invention provides a method of treating anaphylaxis in a patient, comprising administering to the patient two doses of epinephrine from the same device. The method includes injecting (automatically or manually, as described herein) into a patient in need thereof a first dose of epinephrine comprising about 0.15 mL of an epinephrine solution and subsequently injecting (automatically or manually, as described herein) into the patient a second dose of epinephrine comprising about 0.15 mL the epinephrine solution, wherein the total amount of epinephrine delivered between the first and second doses is either 0.3 mg or 0.6 mg. The embodiment of a first automatic injection and a second manual injection has been described in a previous application (Ser. No. 11/175,543). The concentration of epinephrine solution can be, for example, about 0.5 mg of epinephrine per mL of solution, or about 1 mg of epinephrine per mL of solution, or about 1.5 mg of epinephrine per mL of solution, or about 2.0 mg of epinephrine per mL of solution, wherein the total amount of epinephrine delivered between the first and second doses is either 0.3 mg or 0.6 mg. In some embodiments, when the concentration is higher or lower than 1 mg of epinephrine per mL of solution, the volume is adjusted accordingly.

It is necessary that the patient monitor his or her symptoms, or that the person caring for the patient monitors the patient's symptoms directly. In cases where the symptoms of anaphylaxis are not suitably ameliorated by administration of the first injection of 0.15 mL, it will be necessary to administer a second dose. Additionally, in cases where the patient is unable to obtain professional medical assistance before the beneficial effects of the first dose begin to subside, it will be necessary to administer a second dose. The concentration of epinephrine solution can be, for example, about 0.5 mg of epinephrine per mL of solution, or about 1 mg of epinephrine per mL of solution, or about 1.5 mg of epinephrine per mL of solution, or about 2.0 mg of epinephrine per mL of solution, wherein the total amount of epinephrine delivered between the first and second doses is either 0.3 mg or 0.6 mg. In some embodiments, when the concentration is higher or lower than 1 mg of epinephrine per mL of solution, the volume is adjusted accordingly. In certain embodiments, the second dose is administered less than about 30 minutes after the first dose, e.g. less than about 20 minutes after the first dose. In particular embodiments, the second dose is administered less than about 10 minutes after the first dose. In some of these embodiments, the method includes automatically injecting both the first and the second doses with an injection device. In other embodiments, the method includes manually injecting both the first and the second doses with an injection device. In yet other embodiments, the method includes injecting one of the doses automatically, and one of the doses manually, with an injection device, and in particular, injecting the first dose manually and the second dose automatically.

The second dose may be self-administered by the patient or administered by someone other than the patient. In some embodiments, both the first and second dose are self-administered by the patient, both the first and second doses are administered by a person other than the patient, the first dose is self-administered and the second is administered by someone other than the patient or the first dose is administered by someone other than the patient and the second dose is self-administered by the patient.

The smaller dose of epinephrine solution, containing 0.15 mL of a 1 mg/mL epinephrine solution, is especially suitable for treating smaller patients, who may find the larger volume injection of 0.3 mL uncomfortable, painful or intimidating. Thus, in some embodiments in which the dose is about 0.15 mL (i.e. containing 0.15 mg epinephrine), the weight of the patient weighs less than about 30 Kg. In particular embodiments, the patient weighs less than about 15 Kg. While the advantages of the above embodiment are apparent, the concentration of epinephrine solution can be varied, for example, about 0.5 mg of epinephrine per mL of solution, or about 1 mg of epinephrine per mL of solution, or about 1.5 mg of epinephrine per mL of solution, or about 2.0 mg of epinephrine per mL of solution, wherein the total amount of epinephrine delivered between the first and second doses is either 0.3 mg. In some embodiments, when the concentration is higher or lower than 1 mg of epinephrine per mL of solution, the volume is adjusted accordingly.

The smaller dose of epinephrine solution, 0.15 mL, is especially suitable for treating younger patients, especially children, who may find the larger volume injection of 0.3 mL uncomfortable, painful or intimidating. Thus, in some embodiments, wherein the dose is 0.15 mL of USP 1:1000 dilution epinephrine, the patient is a child. In particular embodiments, the child is less than about 12 years old. Alternatively, the dose can be 0.15 mL of USP 1:2000 dilution of epinephrine.

In some embodiments, the invention provides a drug delivery device for treatment of anaphylaxis. The drug delivery device contains sufficient epinephrine solution for injection of at least two doses of epinephrine solution each independently selected from 0.15 mL and 0.3 mL. The concentration of epinephrine solution can be, for example, about 0.5 mg of epinephrine per mL of solution, or about 1 mg of epinephrine per mL of solution, or about 1.5 mg of epinephrine per mL of solution, or about 2.0 mg of epinephrine per mL of solution. In some embodiments, when the concentration is higher or lower than 1 mg of epinephrine per mL of solution, the volume is adjusted accordingly. As will be recognized by those of skill in the art from the disclosure herein: (a) the essential feature of one preferred embodiment of the invention is administration of a first dose of an epinephrine solution containing about 0.15 mg of epinephrine, optionally followed by a second dose of an epinephrine solution containing about 0.15 mg of epinephrine; and (b) the essential feature of another preferred embodiment of the invention is administration of a first dose of an epinephrine solution containing about 0.30 mg of epinephrine, optionally followed by a second dose of an epinephrine solution containing about 0.30 mg of epinephrine. Further, in some embodiments, in addition to epinephrine, the epinephrine solution also contains at least one pharmaceutically inactive ingredient, such as sodium bisulfite as a preservative, a pH buffer, an agent for adjusting osmolality (such as to establish or maintain isotonicity with the tissue in which the solution is to be injected), or a mixture of two or more of the foregoing.

Embodiments of such an automatic injection device are provided in U.S. Pat. No. 5,695,472 and U.S. patent application Ser. No. 11/006,382, filed Dec. 6, 2004, both of which are incorporated herein by reference in their entirety, and are further described herein, as are embodiments for an automatic injection of a first dose and an automatic injection of a second dose; a manual injection of a first dose and a manual injection of a second dose; and a manual injection of a first dose and an automatic injection of a second dose.

Syringe Subassemblies

FIGS. 1 and 2 illustrate syringe subassemblies 10 and 11 that are capable of use with the present invention. The illustrated syringe assemblies or subassemblies 10 and 11 are both of known structure and are commercially available. Exemplary commercial subassemblies are manufactured, sold, or distributed under the trademark CARPUJECT™ by Hospira, Inc. Other subassemblies may also be suitable but may require some modification depending on the specifics of construction.

Both subassembly configurations include an ampule 12 that may be a small glass or plastic vial for containing the aforementioned epinephrine solution. The quantity of the epinephrine solution will be sufficient to deliver at least a full quantity of the first and second doses. Where the two doses to be delivered are each 0.3 mL, the amount of epinephrine solution within the ampule 12 is at least about 0.6 mL, at least about 0.7 mL, at least about 0.8 mL, at least about 1.0 mL or more. In embodiments in which the two doses to be delivered are 0.15 mL, the amount of epinephrine solution within the ampule 12 is at least about 0.3 mL, at least about 0.4 mL, at least about 0.5 mL, at least about 0.6 mL, at least about 0.8 mL or more. The precise amount of epinephrine solution will be determined by the person skilled in the art upon consideration of such factors as syringe dead volume, etc., to meet the criteria of the total amount of epinephrine delivered between the first and second doses to be either 0.3 mg or 0.6 mg.

In both syringe assemblies 10 and 11, the ampule 12 includes a rearward end 13 that is potentially open to slidably receive a plunger 14. The plunger 14 and plunger piston (not shown in this view) can be moved axially within the ampule 12 bore 15 by application of axial force against the plunger shaft 61. The plunger 14 will thus force the epinephrine solution out through a hollow needle assembly 16 at a forward end of the ampule 12 when the plunger 14 is depressed toward the forward or needle end, i.e. toward needle 17 (FIG. 1), 24 (FIG. 2).

Subassemblies 10 and 11 differ in the construction of their needle assemblies 16. Subassembly 10 (FIG. 1) is of the fixed needle variety in which a fixed hollow needle 17 is mounted by a fixed hub 21 to the associated ampule 12. The needle 17 openly communicates with the epinephrine solution within the ampule 12 and will eject the epinephrine solution in response to forced fluid displacing motion of the plunger 14. A sheath 19 may be included to releasably cover the fixed needle 17 for sanitary and safety purposes, and must be removed before administration of the injections.

Needle assembly 16 for syringe subassembly 11 (FIG. 2) differs from the fixed needle assembly structure 10 described above. Syringe subassembly 11 makes use of a double needle assembly 20 in which a double needle hub 90 or 21 mounts a seal penetration needle 22 that projects rearwardly toward a penetrable seal 23 on the associated ampule 12. Flesh penetration needle 24 projects forward. In practice, both needles 22 and 24 can be made integral. In such an integral construction both needles may be formed of the same needle tube, sharpened at both ends and immovably fixed to needle assembly hub 90.

Hub 90 mounts both needles 22 and 24 and has a cup-shaped receptacle for receiving the sealed end of the ampule 12. It also preferably has features or provisions to mount the needles in axial sliding relation to a seal retainer 25 of the associated ampule 12. Forced sliding movement of the ampule 12 relative to hub 90 will thus cause the seal penetrating needle 22 to engage and then pierce the penetrable seal 23. Once seal 23 is pierced, the epinephrine solution within the ampule 12 may be forced through the needle 24 or needles 23 and 24 as the injection is administered.

The double needle subassembly 11 may also make use of a protective needle sheath 19. The sheath 19 can vary or be substantially similar, or even identical to that used for the single needle subassembly 10. For either form of subassembly, the sheath 19 may be provided as a rigid cover, as disclosed in earlier issued U.S. Pat. Nos. 5,540,664 and 5,695,472; such disclosures being hereby incorporated by reference into this application. Also incorporated by reference are earlier U.S. Pat. Nos. 5,358,489 and 5,665,071.

Injection Device

General Configuration

Description of the device herein includes application to a device for a first automatic injection and a second manual injection. A hypodermic injection device 30 according to the invention is shown in the drawings. Injection device 30 (FIGS. 3-6) includes a barrel 31 having a muzzle end 32, with a needle receiving aperture 34, which is a passageway allowing passage of the needle 17, 24. A syringe subassembly receiving cavity 35 is situated along and within the barrel 31 and is preferably adjacent to and accessible from the muzzle end 32. The cavity 35 is adapted to releasably and slidably receive a syringe subassembly 10 or 11 for movement toward and away from the muzzle end 32. The needle assembly 16 is aligned to project through the needle receiving aperture 34.

A syringe driver 36 has an actuator or driver contact 37 that is movable toward the muzzle end 32 extending into the syringe subassembly receiving cavity 35. A penetration controller 38 or other penetration controller 38 is also advantageously provided. The penetration controller 38 may include a penetration controller 38 abutment surface 39 which engages the ampule 12 assembly, such as at a shoulder or other appropriate feature thereof. The penetration controller 38 has a suitable length and configuration from the muzzle end 32 to provide a desired needle penetration depth or forward needle stop position.

The Barrel

As set forth by example in the drawings, barrel 31 is elongated and tubular, defining the subassembly receiving cavity 35 between a rearward end 41 and the muzzle end 32. The barrel 31 may be formed of plastic or another suitable medically acceptable material of suitable strength.

A driver guide or driver spring guide 33 can be integral with or fitted as a sleeve within the barrel 31 to maintain the driver spring 36 or other driver force generator in a desired position, such as coaxially positioned therein. As shown, driver spring guide 33 functions to guide extension and retraction of the syringe driver spring 36. Driver spring guide 33 as shown also advantageously functions as a positioner to accurately locate the syringe assembly 10, 11 coaxially within the barrel 31.

In the illustrated embodiments, the rearward barrel end 41 is adapted to mount firing bushing 43, which is an annular end piece, and which is used in conjunction with the driver 36, details of which will be described further below. To facilitate assembly, the rearward barrel end 41 is preferably molded about an inward annular ridge 44. It may alternatively be possible to produce each part separately and have the annular ridge 44 snap fit with the firing bushing 43.

The muzzle end 32 mounts a separable nose cap 45 that includes the needle aperture 34 or other passageway through which the forward needle 17 extends when fired. The aperture 34 of the nose cap 45 is attached to the barrel by means of inter fitting threads 46, rings or other projections, which together allow the nose cap 45 to be removed from the muzzle end 32. The nose cap 45 may thus be separated from the barrel to permit access to the barrel cavity 35, thereby permitting insertion and removal of the needle subassemblies 10 or 11.

Syringe Driver Subassembly

Driver 36 is used to operate against or be connected through a plunger rod 61 to the plunger 14 of the needle subassembly 10 or 11. The plunger rod 61 may be separable or integral with the plunger 14, which acts as a piston to push epinephrine solution through the inner lumen of the syringe 10, 11 and out the needle 17. The driver 36 is able to force the subassembly in a forward direction to effect needle penetration and to operate against the plunger 14 to inject the epinephrine solution contents of the ampule 12. Such forces are automatically applied by spring or other suitable driver force initiated through a triggering operation initiated by the user.

Driver 36 as exemplified herein includes the driver bar 37 or shaft 37 (FIGS. 3, 4) which is shown within the barrel 31 in a rearwardly cocked position by a driver release mechanism 53 that may be similar or identical to that shown in U.S. Pat. Nos. 5,540,664 and 5,358,489, both of which are incorporated by reference herein.

Notwithstanding the above incorporated materials, a suitable driver is further exemplified herein as including a drive spring 50 that is compressed when ready or cocked. The drive spring 50 is preferably guided and contained within the barrel by a spring guide which is advantageously in the form of a guide sleeve 51. As shown, the guide sleeve is tubular with the guide spring extensible within tubular guide sleeve 51 with portions of the spring 50 being able to slide within the guide sleeve 51. Other configurations may also be suitable.

The drive spring 50 is selected to provide sufficient stored energy, when compressed, that when it is released it can force the needle subassembly forwardly against downstream resistance and perform needle penetration and injection functions. It serves to displace the plunger 14 and thus expel the medicament contained in the ampule 12 through the injection needle 17.

The drive spring 50 acts against and is restrained by the firing bushing 43 at one end. The opposing end bears upon the driver bar 37 which engages the plunger rod 61. The exemplified driver bar 37 (which in this view is a shaft) provides a spring engagement shoulder 52 (see FIG. 3) against which the forward end 51 of driver spring 50 engages. As shown, driver release 53 includes a barb or barbs 54 that fit through the firing bushing central aperture 114. The barbs 54 are preferably formed on flexible ends of the driver release 53, which are like legs on the driver bar 37.

A safety, advantageously in the form of a safety cap 55, has a forwardly projecting pin 56 that is received between the leg-like portion of the driver release 53 to hold the barbs 54 in engagement with the firing bushing 43 and thereby prevent forward movement of the driver bar 37 through the aperture 114 until the safety 55 is removed. The safety or safety cap 55 can be pulled rearwardly to slide the tapered safety pin 56 from between the legs of the driver bar 37. This frees the barbs to be forced inwardly and radially together. As shown, the barbed legs of driver bar 37 are moved inward by the rearward or end of firing sleeve 57 as will be further detailed below. The firing sleeve 57 acts as a trigger.

Figure 20:
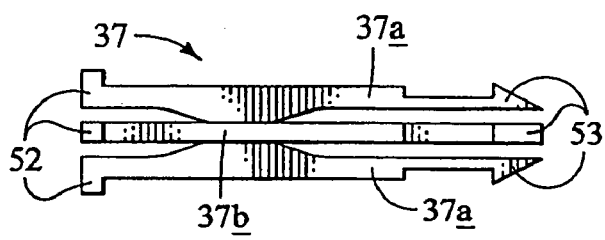
FIG. 20 is a side view of a driver bar construction having four legs.
Figure 21:
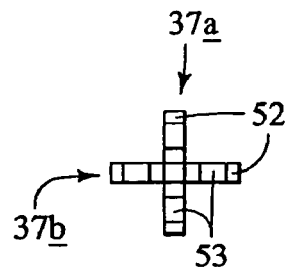
FIG. 21 is an end view of the driver bar of FIG. 20.

FIGS. 20 and 21 show an exemplary driver bar 37 having four legs comprising the release 53, although other numbers are believed possible. In some embodiments, the driver bar 37 is preferably made using two parts 37a and 37b which fit together. These parts 37a and 37b can alternatively be made of metal and be molded or otherwise formed as an integral piece.

Radial inward movement of the barbed legs of release 53 causes the barbs 54 to move into a release position as effected by an exterior firing sleeve 57. In the design illustrated, the firing sleeve 57 extends over and along the outside of the barrel. The exposed length of the firing sleeve allows the user to grasp the injector by the firing sleeve when the injection is to be administered.

A forward end of the firing sleeve 57 can include slots 58 (see FIGS. 4-6, 9 and 10) that slide along retainers 59 formed on the forward end of the barrel 31. The retainers 59 are advantageously in a peninsular configuration that provides flexibility to retainers 59 for assembly or possible disassembly. The interaction between retainers 59 and slots 58 prevent the firing sleeve 57 from being unintentionally removed from the barrel 31. Such interaction also limits the extent of axial relative movement while also allowing the parts to be assembled or disassembled by depressing retainers 59.

The firing sleeve 57 includes a trigger head having an opening 60 (FIGS. 3-6) which is preferably centrally located. The trigger head of sleeve 57 is advantageously beveled along the contact area with barbs 54. Opening 60 receives and inwardly cams the barbs 54 on the legs of the driver bar 37. This forces the barbed ends together once the safety cap is removed and the firing sleeve is moved forwardly with respect to the barrel. Such action triggers the driver release 53 to free drive spring 50. Drive spring 50 thus extends longitudinally, driving the driver bar 37 into the plunger shaft and forcing the syringe subassembly forwardly to administer the injection.

FIGS. 3-6, 7 and 8 show that the driver bar 37 is configured to push against an adjustable plunger rod 61 which is attached to the plunger 14. The plunger shaft assembly may be part of the syringe subassembly 10 or 11. Alternatively, the plunger shaft or rod 61 may be produced as an integral part of the driver or as a separate assembly or part. The plunger shaft may also be made in a non-adjustable configuration, such as solid or as a non-adjustable assembly.

In the illustrated embodiments, the plunger rod 61 is advantageously made up of two axially adjustable components including an actuator or driver engaging section 62 and a plunger engaging section 63. As shown, sections 62 and 63 are engaged via threads to allow for adjustment of the overall length of rod 61. In some embodiments, this is used to help adjust the dosage or volume of material dispensed during a single operation of the injection apparatus.

The illustrated plunger rod 61 is advantageous in that the two axially adjustable sections 62, 63 allow for longitudinal rod length adjustment, and for threaded or other connection to the plunger 14. Section 62, as shown, has a head portion and threads which are received into section 63. Plunger rod 61 section 63 is coupled, such as by threads, or is otherwise attached to plunger 14. Relative rotation of the two sections 62 and 63 can effectively change the length of plunger rod 61, thereby allowing for accurate dosage adjustment, even though the syringes vary in length until adjusted to have the same or other desired length.

It is also possible that a different, conventional form of plunger rods (not shown) might be provided as a part of the syringe subassemblies 10 or 11. In such an alternative construction the adjustable rod 61 may not be needed or used. In such a construction, dosage adjustment may be made sufficiently accurate by using a properly selected stop collar 64, discussed further below. In either construction, plunger rod 61 or an alternative integral plunger rod (not shown) can be provided with or as a part of the plunger assembly. With an adjustable plunger rod 61, such as provided by parts 62 and 63, dosage control is more accurate since each ampule 12 may vary in length and the adjustment capability can accommodate for such variations.

Dosage Adjustment

The automatic injection device according to the invention is capable of use for single or for multiple (i.e., two) injections. To enable such use, one or more stops in the form of dose stop collars 64 (FIG. 7) can be releasably mounted to the driver 36 or, as in the illustrated example, to the plunger rod 61. In the illustrated embodiments, one such collar 64 is shown attached to the rod 61 rearward of the ampule 12, and forward of the headed section 62 of the plunger rod 61. The collar 64 and possible multiple such collars are advantageously positioned in the forward path of the headed end of the plunger rod 61. Collar or collars 64 stop forward motion of the plunger rod 61 at such point where a selected first dosage (0.3 mL or 0.15 mL of epinephrine solution) has been expelled from the syringe subassembly 10 or 11. For example, for applying two automatic doses of medicine from the same device, the stop collar 64 is used for the first dose injection (FIG. 7) and the device can be used for the second dose injection after removal of the stop collar 64 (FIG. 8). After injection of the first dose (0.3 mL or 0.15 mL of epinephrine solution), a second dose remains within the ampule 12 following the first injection. The syringe subassembly 10 or 11 can be removed from the barrel 31 to gain access to collar 64, which then can be removed from the plunger rod 61 to permit further motion of the plunger 14 to deliver the additional dose.

The second dose can be either an automatic injection or a manual injection. If the second dose is an automatic injection, in some embodiments of the invention it may be necessary to disassemble and reassemble the device after the removal of a designated stop collar. "To disassemble the device" refers separation of the nose cap subassembly (described below) and the syringe subassembly from the rest of the device, i.e., the barrel and the syringe driver subassembly. "To reassemble" refers to installation of the syringe subassembly and the nose cap subassembly (described below) with the rest of the device, i.e., the barrel and the syringe driver subassembly, through connection means as described herein. The syringe driver subassembly components, including a driver spring 36, a driver spring guide 51, a firing bushing 43, a driver bar 37, a driver release 53, and a safety cap 55 with a projecting pin 56, need to be connected to positions as shown in FIG. 3 or 5. The device is now ready for the second dose automatic injection.

If the second dose is a manual injection, there is no need for a reassembly. Following removal of the syringe and collar, the syringe 10 or 11 can be used to inject the second dose of epinephrine solution manually. The needle is first inserted subcutaneously or intramuscularly into the patient. The plunger rod 61 is then pressed with the thumb or other digit in the direction of the needle 17, thereby ejecting epinephrine solution (0.3 mL or 0.15 mL) into the patient.

The length dimension of the collar 64 can be selected according to the desired dosages to be administered. Stop collar 64 may be made having different sizes of arcs. In some cases the collars extend fully about the plunger shaft. A currently preferred stop collar has an arcuate size of about 180-200 arcual degrees. FIGS. 16 and 17 show a currently preferred design having an open side and an arcuate size 110 of about 185-190 arcual degrees. The relatively open side 111 is advantageously provided with end faces 112 which are beveled to converge inwardly. These features provide easier installation of the stop during production and easier removal by a user after the first or other prior dose has been administered. In some embodiments of the invention, it is possible to remove a designated stop collar without disassembling and reassembling the device, which will be apparent to one of skill in the art, for example by generally making a stop collar accessible for removal from the outside of the device, whereby the stop collar is removed by a user after a first use. The device is then ready for the second dose injection.

Another feature shown in FIGS. 16 and 17 that facilitates removal of stop collar 64 is the provision of ribs, flutes, striations or other friction features 120. These friction features improve manual grasping of the collar to remove it from the outside of plunger shaft 61. This construction allows a user to remove the collar using the thumb and forefinger from a single hand. It improves the removal such that two hands are not necessary as was the case in earlier embodiments. This improvement greatly reduces the chance that the action of removing the stop collar does not lead to accidental depression or upward movement of the plunger 14 which may compromise the accuracy of the second dose amount.

The outside of the stop collar 64 may also advantageously be provided with circumferential segments 121 between the friction features 120 and a flat segment 122. Flat segment 122 facilitates installation of the stop collar upon the plunger rod 61.

The inside surface 124 is preferably semi-cylindrical and sized to fit the plunger rod 61. The particular size may vary depending on the size of ampule 12 and size and type of plunger rod 14 used.

Nose Cap or Muzzle End Piece

FIG. 6 shows that nose cap 45 is advantageously removable from the barrel 31 to allow insertion and removal of a syringe subassembly 11. It is especially desirable that the nose cap 45 be removable to allow extraction of the syringe subassembly 10 or 11 to allow manual injection of epinephrine solution as described herein. Cap 45 may be generally in a cup shaped form to be received upon the forward end of barrel 31. In the illustrated embodiments, the nose cap 45 fits over the outward surface of the barrel 31. The nose cap 45 is secured thereon using threads 46 or other suitable connection joint. Depending on the specific construction used, the nose cap 45 may alternatively fit within the barrel 31.

It is preferred for accuracy in needle penetration depth control that the nose cap 45 be secured axially against a positive stop such as a shoulder 47 formed along the barrel 31. Shoulder 47 can be provided along the barrel 31 to accurately locate an installed nose cap 45 in a repeatable manner. This is preferred to provide axial accuracy to the relative location of the nose cap 45 upon the barrel 31. This is desirable since the nose cap 45 may be removed and re-mounted repeatedly to enable removal and replacement of ampule 12 and needle subassemblies 10, 11.

It is advantageous for accurate positioning of the nose cap 45 to use the threads 46. Threads 46 are provided along the nose cap 45 and barrel 31 to facilitate secure engagement between the abutment shoulder 47 and nose cap 45. However, fastening arrangements between the nose cap 45 and barrel 31 may be used other than the illustrated threads 46. For example, a bayonet, barb, snap fit or other releasable connection arrangement could also be used to releasably interlock the nose cap with the adjacent forward part of barrel 31 to provide repeated accurate positioning.

The forward end of nose cap 45 defines the illustrated needle aperture 34, which is advantageously sized to receive needle sheath 19 therein. As illustrated in FIGS. 9 and 10, the needle safety sheath 19 can project through the aperture 34. Sheath 19 may be provided with a blunt forward end which may extend forward of the muzzle end 34. The projection of the sheath 19 facilitates removal of the sheath 19 immediately prior to use.

The outside of nose cap 45 may advantageously be provided with ribs, flutes, striations or other friction surface to facilitate installation and removal of the nose cap 45 from the barrel 31. The construction shown uses a threaded connection between the nose cap 45 and barrel 31. Thus an exterior friction surface allowing torque to be applied is preferred in such constructions. A preferred friction surface has minute linear longitudinal striations (not shown).

Sheath Remover 80

Description of the device herein is also applicable to device for a first automatic injection and a second manual injection disclosed in a previous application (Ser. No. 11/175,543). Removal of the sheath 19 from the syringe sub-assembly 10 or 11 can be accomplished or facilitated by provision of a sheath remover 80 that is releasably mounted at the muzzle end 32. FIG. 18 shows an exemplary sheath remover 80 from the forward end. FIG. 19 shows a side view of the sheath remover 80. The construction illustrated includes a sheath 19 gripper 81. The gripper has a central aperture 85 that is disposed in substantial coaxial relation to the needle receiving aperture 34 of the nose cap. The central aperture 85 receives the sheath 19 therethrough.

Gripper 81 also preferably includes radially inward projecting fingers 82 that flexibly grip the sheath 19 behind a lip 89 (see FIG. 3) near the tip of the sheath remover 80. The inwardly projecting fingers 82 provide sufficient flexibility to allow the sheath remover to be pushed onto and installed over the enlarged end of the sheath 19 near lip 89.

A collar portion 84 extends rearwardly of the end surface 87 and is received over the nose cap 45. The collar portion 84 may be provided with circumferential ribs 83 to improve manual grasping of the sheath remover 80 so as to facilitate pulling the sheath 19 and sheath remover from the injector.

Fingers 82 will flex rearwardly during removal of the sheath 19 and catch on lip 89 and securely grip the sheath 19 when the sheath remover 80 is pulled forwardly, In doing so, the fingers will catch behind the lip and further bind and pull the sheath 19 from the needle assembly hub 90 (FIG. 3) to expose the outwardly directed needle 17. The sheath 19 and sheath remover 80 can later be re-installed, in an instance where it becomes desirable to re-cover the needle for safety purposes.

Penetration Controller 38

Description of the device herein is also applicable to device for a first automatic injection and a second manual injection disclosed in a previous application (Ser. No. 11/175,543). Syringe driver 36, when triggered, forces the syringe subassembly 10 or 11 forward within barrel cavity 35. This drives the needle 17 forward through the aperture 34 to penetrate the flesh of the patient. Depth of penetration according to the present invention is advantageously determined using a penetration controller 38 (FIGS. 9-15) and other alternative forms described herein. The penetration controller 38 stops penetration at a desired repeatable penetration depth of needle 17. This is different than dose control, since the penetration depth is gauged from the nose cap 45 which actually contacts the flesh during automatic injection.

Penetration controller 38 in preferred forms is located along the barrel 31, with an abutment surface 39 spaced from the muzzle end 32 at a selected and desired needle penetration depth stop position. The penetration controller 38 is engaged by the syringe assembly to stop forward motion of the flesh penetration needle 17 at the selected penetration depth. This is done to remove the necessity for the user to determine penetration depth. By providing a penetration controller 38, the device can be selected or adjusted so the needle will penetrate only to a desired depth as an automatic function of the device. Adjustment is preferably provided using a penetration sleeve, spring or other penetration controller 38 element.

First Exemplary Penetration Controller 38

Figure 22:
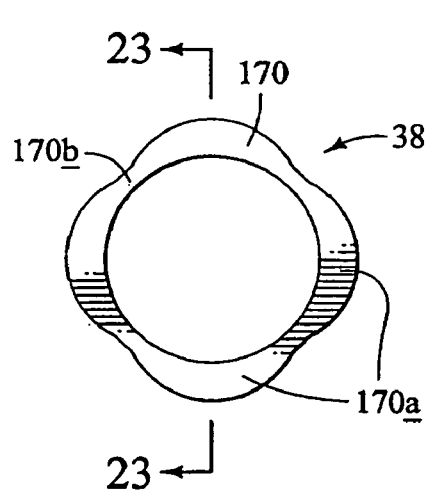
FIG. 22 is an end view of a preferred penetration controller 38 sleeve.
Figure 23:
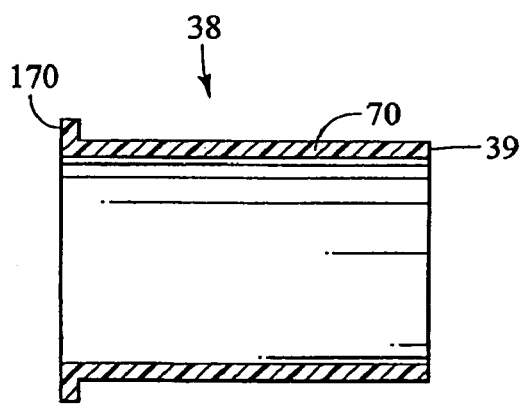
FIG. 23 is a side sectional view of the penetration controller 38 sleeve of FIG. 22 taken along section line 23-23 of FIG. 22.

Description of the device herein is also applicable to device for a first automatic injection and a second manual injection disclosed in a previous application (Ser. No. 11/175,543). In one preferred form, the penetration control is provided by penetration controller 38. Penetration controller 38 may be constructed more specifically in the form having a tubular sleeve 70 portion held within the nose cap 45. FIGS. 22 and 23 show penetration controller 38 in detail. The penetration controller 38 includes a control sleeve 70 which has a flange 170 attached thereto. It is advantageous that the sleeve 70 and flange 170 be shaped for frictional engagement within the nose cap 45. This is desirable so that removal of the nose cap 45 will also result in removal of the penetration controller 38. This is facilitated by flange lobes 170a which tend to cant within the nose cap 45 cavity (FIG. 22). This mounting arrangement also helps to provide repeatable and accurate axial positioning of the abutment surface 39 within the barrel 31 and relative to the outer front face of the nose cap 45 or other flesh contacting face of the injector. The flange sleeve 70 and thickness of flange 170 define the length of the controller 38. The end of the sleeve 70 opposite the flange provides a syringe abutment surface 39 at a selected distance from the muzzle end. In this example, the surface 39 is at the rearward end of the sleeve 70 and faces the needle subassembly 11 within the cavity 35.

The overall length of controller 38 is typically defined by the length of sleeve 70. The length may be selected from a group having varying axial dimensions to effect different needle penetration depths. Thus one sleeve 70 may be useful for subcutaneous injections, while another may be selected when deeper intramuscular penetration is required. A selection of sleeves 70 of differing axial lengths may be used dependent upon the medicine being provided in the injector or for specific depths of desired needle penetration.

The sleeve 70 is also useful to receive a forward or return spring 71, preferably of the coiled compression variety, which can be disposed within the barrel 31, between the nose cap 45 and needle hub 90. The front or return spring 71 is provided to yieldably resist forward motion of the needle subassembly 11 to hold the subassembly 11 in the retracted position until the syringe driver 36 is triggered. Return spring 71 also helps to reduce the impact of the syringe assembly with the penetration controller 38, thus reducing or eliminating breakage of the hub 21 or penetration controller 38.

Nose Cap Subassembly

Description of the device herein is also applicable to device for a first automatic injection and a second manual injection disclosed in a previous application (Ser. No. 11/175,543). The penetration controller 38 can be used to secure the return spring 71 in position within the barrel 31, using flange 170. This also helps retain the return spring 71 for removal along with the nose cap 45 (FIG. 13). To this end, the spring diameter may be enlarged at its forward end 72 in order to provide a friction fit between the spring 71, sleeve 70 and the nose cap 45, while allowing the remainder of the spring free movement within the confines of the sleeve portion 70.

One of the important functions of the return spring 71 is to keep the needle 17 in a hidden, retracted position after the sheath 19 is pulled off. This prevents the user from seeing the needle 17 and prevents the user from being scared due to needle fright. The return spring 71 acts quickly on removal of the sheath 19 to return the syringe 11 up inside the barrel 31 such that the user has no visual reminder that there is a needle 17 positioned in a hidden position therein.

By providing the return spring 71 and sleeve 70 arrangement described above, the fully compressed axial spring length will be less than the sleeve 70 length. Thus the penetration depth is determined by the selected length of sleeve 70 and flange 170. With proper design, the yieldable resistance offered by spring 71 will remain within suitable limits regardless of the sleeve 70 length selected to adjust penetration depth.

The above arrangement (in which the return spring 71, selected sleeve 70 and flange 170 and nose cap 45 interconnected) is advantageous to simplify attachment to and removal from the barrel 31. A user wishing to gain access to the needle subassembly 11 for replacement or for second injection purposes, need only unthread the nose cap 45 from the end of the barrel 31. The return spring 71 and sleeve 70 will move along with the nose cap 45 to permit free access to the cavity 35. The lobes 170a also may interact with the internal threads of the nose cap 45 to help prevent the nose cap 45, sleeve 70 and front spring 71 from flying freely when disconnected from the barrel 31.

Second Exemplary Penetration Controller 38

Figure 15B:
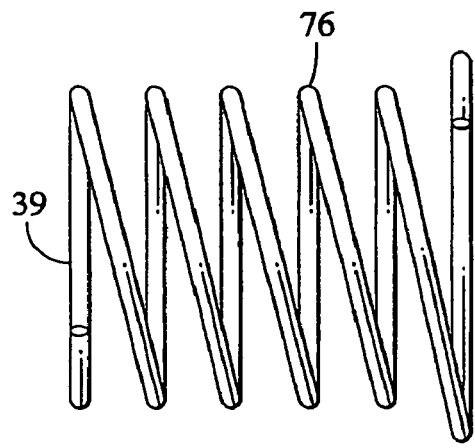
Figure 15C:
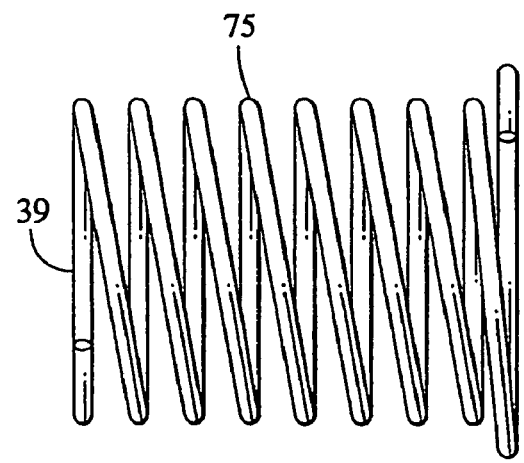

Description of the device herein is also applicable to device for a first automatic injection and a second manual injection disclosed in a previous application (Ser. No. 11/175,543). Another form of the penetration controller 38 may be provided in a form and construction which uses a selected spring 71 of a particular fully compressed length dimension. FIGS. 15A-15C illustrate by way of example several springs 75, 76, 77 that will have different fully compressed lengths but similar lengths when installed in device 30. In each one of the springs, one of the spring ends will function as the abutment against which the needle hub 21 engages or other parts engage as explained further below. The needle hub 21 will stop when the spring 71 is fully compressed and the desired penetration depth is attained.

By using a spring 75, 76, 77 that is selected for a desired compressed length, the spring itself becomes the penetration controller 38 when fully compressed between the needle hub 21 and the nose cap 45. Thus the spring can have dual functions: offering yieldable resistance to slow forward motion of the adjacent needle subassembly; and stopping such forward motion once the needle reaches the selected penetration depth and the spring becomes fully compressed.

Figure 15D:
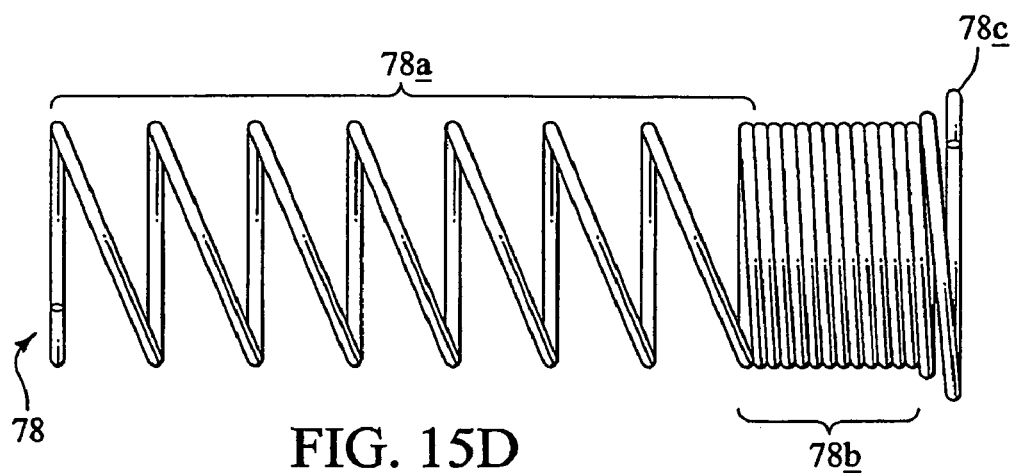
Figure 15E:
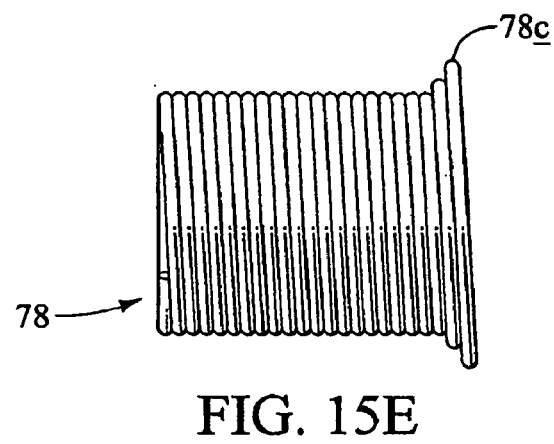
Figure 15F:
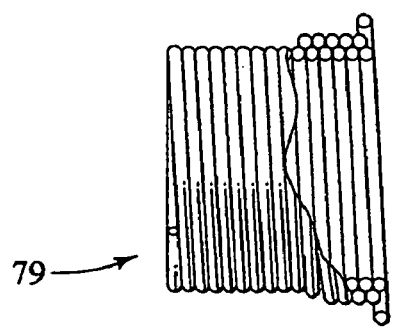

The selected springs 75-77 can be made to fit frictionally within the nose cap 45 in order to keep the spring 75, 76, 77 and nose cap 45 together. This simplifies access to the cavity 35 and a needle assembly 11 therein. It also mitigates flying discharge of the nose cap 45 and spring 71 when disconnected. Thus, the cap 45 and spring 71 can be assembled so both can be simultaneously removed from the barrel 31 as a unit. Changing from one spring to another to accommodate different penetration depths is a simple matter of removing the nose cap 45 from the barrel 31 and changing the spring 75-77. Alternatively, an assembly including a nose cap 45 and different spring 75-77 can be used to change penetration depth, FIGS. 15D, 15E and 15F show additional novel concepts in using the forward spring for penetration controller 38 and absorption of energy from the moving drive and syringe assembly. FIG. 15D shows spring 78 in a free and uncompressed condition. Spring 78 has three sections, 78a, 78b and 78c. Section 78a has spaced helical or spiral windings which may be collapsed due to force applied by the driver 36 through the syringe assembly 11. Section 78b includes one or more dead windings which are close or tight and are normally not compressible due to application of axial compressive force to spring 78. Section 78c is enlarged end coils or windings that are radially contracted when installed in the nose cap 45 receptacle and serve to tie the spring 78 and nose cap 45 together.

By adjusting the relative proportion of sections 78a, 78b and 78c, the compression and energy absorption properties of the forward spring 78 can be adjusted to provide different penetration controller and different deceleration characteristics. More dead coils reduce energy absorption as the forward spring 78 is compressed because there are fewer active coils to absorb energy. Thus, the increase in the number of dead coils causes less energy to be absorbed by the forward spring and allow the driver to better maintain energy sufficient to inject and dispense the medication.

FIG. 15E shows spring 78 in a fully compressed but axially aligned and stacked condition. This occurs when the spring 78 has stronger and/or large spring wire. The spring 78 made with stronger wire will thus reach a fully compressed state and then relatively abruptly stop at the demonstrated penetration depth for that design of spring 78.

FIG. 15F shows a spring 79 similar to spring 78 with similar sections. Spring 79 does, however, demonstrate a different type of behavior upon full compression. The spring wire is made finer and less strong. This causes the spring 79 to compress and then distort into a distorted collapsed condition. This condition provides a two-stage compression action. In the first stage or phase, the spring 79 compresses in a typical or nearly typical stack arrangement. In the second stage or phase, the spring 79 distorts with various windings being forced to radially change, thus distorting and collapsing with some winding either moving inside of other windings or overriding other windings. This construction effectively provides shock absorption and energy absorption capabilities that reduce shock after the spring has been fully compressed and allow energy absorption after full compression into a stacked array and helps or eliminates breakage of the syringe hub 21 and other parts of the injector 30. It also provides cushioning as the syringe and driver 36 decelerate to a stopped condition.

As examples, springs made of wound or coiled music wire having wire diameter size of about 0.015 inch tend to collapse and distort as indicated in FIG. 15F. In comparison, springs wound from music wire having a diametrical size of 0.018 inch tend to remain in a stacked coil array as indicated in FIG. 15E.

These are current preferred wire sizes for injection devices using only a spring as the penetration controller 38. Although such constructions are not as precise in demonstrating consistent penetration depth, they are sufficiently consistent for the administration of many medicines. They also are more economical to produce and eliminate the penetration controller 38 having tubular sleeve 70 and flange 170 or other similar relatively inelastic penetration controller 38 elements. They are also less expensive to produce and assemble.

Use of finer spring wire has another beneficial effect. The springs tend to distort more easily and further reduce the risk that a nose cap and spring assembly fly away upon removal, such as when preparing for administration of a second or subsequent dose.

Syringe Assembly Front Spring Load Distribution, Guidance & Cushioning

Description of the device herein is also applicable to device for a first automatic injection and a second manual injection disclosed in a previous application (Ser. No. 11/175,543). FIGS. 24 and 25 show front portions of an injection device 30 having many of the same features as described elsewhere herein. Description of the common features are made using the same reference numbers and the description which is common will not be repeated.

The embodiment of FIGS. 24 and 25 differ in that a load distribution ring 171 is provided to act in several capacities. The first capacity is to distribute the forces developed between the front spring 75 and the syringe, particularly at the syringe assembly hub 21. The second capacity is to act as a guide piece to help maintain the coaxial position of the syringe assembly hub 21 within the barrel cavity 35. The third capacity is to also distribute and equalize force about the annular abutment 170 so that the forces developed against the syringe are not concentrated.

The ring 171 is preferably made about the same size as the barrel cavity 35 portions within which the load distribution ring 171 (acting as a guide ring) moves during operation of the injector. This is advantageously done by making the ring within a range of about −0.001 inch to about −0.004 inch compared to the adjacent barrel cavity 35 interior diameter. Other size relationships are also believed operable.

Ring 171 is preferably made from a stainless steel or other suitable material which is strong and sufficiently stiff to help distribute the load evenly which is applied across the ring.

FIGS. 24 and 25 further show a resilient cushion in the form of a cushion or pad ring 172 which surrounds the syringe hub 90. The cushion is preferably made from an elastomer material such as natural rubber or Santoprene 8281-45-med having a durometer value of about 45. In the uncompressed state the cushioning pad ring 172 is about 0.030 inch smaller in diameter than the load distribution piece 171. This allows the pad ring to expand outwardly in a radial direction when load is applied thereto as the syringe is driven against the front spring 75 and resistance is developed in association with dispensing the fluid medication from the front needle 24. An outer diameter which is larger and closer to the adjacent barrel internal diameter may lead to lateral strain that causes the pad ring 172 to develop frictional drag against the barrel bore 35. This in turn requires more driver force to be provided in order to overcome the friction and creates added stress and strain on the syringe and other parts of the injector.

Figure 26:
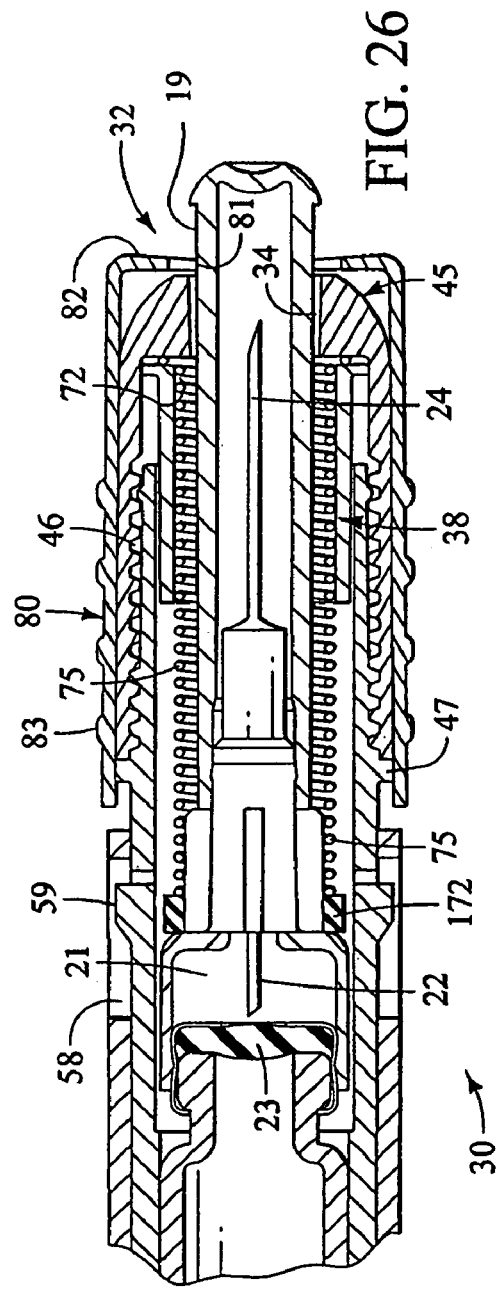
FIG. 26 is an enlarged partial side sectional view of another preferred form of the invention in a cocked condition with needle retracted.
Figure 27:
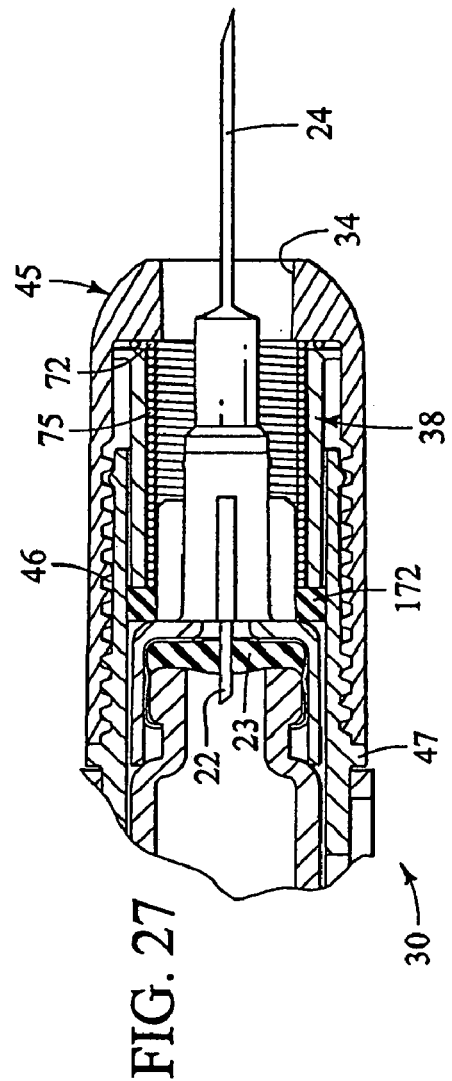
FIG. 27 is a partial view similar to FIG. 26 with the injector shown with the syringe assembly in an extended position.

FIGS. 26 and 27 show another embodiment similar to that shown in FIGS. 24 and 25. The embodiment of FIGS. 26 and 27 is not provided with a load distributor and guide ring like ring 171 of FIGS. 24 and 25. Instead, the cushion pad 172 directly bears on the syringe hub 21 and the front spring 75. Although this construction is not as preferred as that shown in FIGS. 24 and 25, it is believed operable. Due to the less uniform load application a harder and more durable elastomer material may be needed to allow repeated use of an injector 30 so constructed.

In either of the constructions shown in FIGS. 24-27, the cushion pad 172 has been found to be superior at moderating forces experienced by the syringe hub 90 and thus reduces the risks of failure or breakage of the hub 90 or other portions of the syringe assembly.

Summary of Front Return Spring Functions

The front or return spring thus performs a number of important functions in certain embodiments of the invention. It maintains the syringe assembly in a retracted position prior to use, such as during, carrying by the user and other situations. Any one of these may by routine or accident cause force to be developed on the syringe and return spring. The return spring thus maintains or helps to maintain the syringe in a retracted position prior to firing but does so in a manner that absorbs shock and minimizes the risk of syringe ampule 12 breakage.

The return springs also serves to help keep the injection needle up inside the nose cap or barrel 31 to keep it in a hidden position to prevent user alarm at sight of the needle.

Another function of the return spring is to counteract against the drive spring upon triggering of the injection. The drive spring accelerates the syringe down the barrel 31 and the kinetic and well as stored spring energy is preferably dissipated to prevent or reduce the risk of syringe ampule 12 breakage or breakage of other components of the forward end of the injector which in one way or another must take the force and dissipate the energy. Dissipation of energy is particularly enhanced when the spring deforms as illustrated in FIG. 15F.

Another important aspect of the forward or return spring is in some embodiments to provide for proper insertion of the seal insertion needle 22 into and through the ampule 12 seal 23. This is accomplished by selecting a return spring which may provide for delayed administration of the medicine until the needle penetration depth is proper.

In some forms of the inventions the front or return spring may by itself serve as the penetration controller 38. This simplifies the construction of the injector and saves costs where the required consistency of penetration controller 38 for the medicine being used is within the demonstrated consistency of the penetration controller 38 spring being used is satisfactory. Where these parameters are met the more complex penetration controller 38 sleeve 70 can be eliminated.

A still further advantageous function of the front return spring is to hold or help hold the spring with the nose cap. This is accomplished in the illustrated embodiments by using a spring which has enlarged coils toward the forward end. These larger coils serve to maintain the spring with the nose cap when the nose cap is removed. This may prevent or minimize any risk of the nose cap and spring flying off. This property of retaining the spring and nose cap also simplifies handling the nose cap by keeping the nose cap, spring and any tubular penetration controller 38 together as an assembly.

Thus it can be seen that the front return spring performs a surprising number of different functions and advantages or combination of different functions and combinations of advantages.

Considerations for Double Needle Syringe Subassembly

Description of the device herein is also applicable to device for a first automatic injection and a second manual injection disclosed in a previous application (Ser. No. 11/175,543). Description to this point has been generic with respect to the subassemblies 10, 11 because both needle forms can be utilized with the structure described. With respect to the double needle subassemblies, however, the penetration depth controller 38 and the syringe driver 36 are configured to perform an additional function of penetrating the seal 23 using penetrating needle 22.

The seal penetrating task is accomplished as the triggered syringe driver 36 forces the needle subassembly 11 forward. As the subassembly 11 moves forwardly, the hub 21 slides into abutment with the syringe abutment surface 39 of the penetration controller 38. Continued applied force will cause the associated ampule 12 to slide on forwardly although the hub 21 and needles 22 will remain axially stationary in relation to the abutment 39. The forward moving ampule 12 will thus be penetrated by the rearwardly projecting needle 22.

It should be appreciated that tissue penetration depth is not derogatorily affected by the ampule 12 piercing operation. The forward needle 24 will move toward the selected penetration depth as the hub 21 moves to engage the abutment surface 39. Continued forward force against the syringe subassembly 11 by the driver 36 will cause the injection needle 24 to continue being extended as the rearward needle 22 penetrates seal 23. Hub 21 is thus seated as full penetration of the forward needle 24 occurs. Further movement of the driver 36 causes the ampule 12 medication to be dispensed and injected.

The double needle subassembly 11 may in some cases be preferable to the open communication single needle subassembly 11. This can be visualized in that the injection needle will be fully or almost fully penetrated into the flesh before the injected medicine is dispensed into the flesh. With the single needle syringe there is a potential effect of putting medication above the final needle injection depth. So in actual operation the double ended needle may provide more controlled and/or reproducible dispensing of the medicine at the final needle depth. This is what is done in the hospital setting with a manual injection in that the doctor or nurse first places the needle to the desired depth and then presses the plunger. It also prevents loss of medicine as the injection needle passes through intermediate tissue.

The wire diameters for some return springs are suitable for achieving the seating and desired insertion of the ampule 12 by needle 22 at the same time the injection needles reach their desired final penetration depth. This is caused by the springs either being weak enough (lower spring rate) so that the penetration controller sleeve 38 performs the final seating and insertion of needle 22 through seal 23. In other embodiments, such as when the penetration controller 38 is solely by the spring, the spring rate of the return spring is selected to similarly provide for seating and insertion of needle 22 through seal 23 also at or near the desired final penetration depth. In either case, this provides proper administration into the tissues which are the intended tissue for the desired final penetration depth.

The injector also performs another important novel function when used with double needle syringe assemblies, such as 11. Such assemblies require the needle assembly 11 to be seated manually or with a device holder before performing manual injections. The action of firing the injector carrying a double needle syringe causes the needle assembly 11 to seat or mate with the sealed ampule 12. Thus a manually useful syringe is automatically formed. This indicates the multiple functions provided by injectors described herein. One function is to automatically administer the first dose. Another function is to seat the double needle syringe assembly 11 with the sealed ampule 12 to form a manually administrable syringe from a dual needle syringe and sealed ampule 12. A further function is to provide a reliable backup syringe for situations where the syringe may be misused and the second dose is the only dose and can be administered manually for ultimate reliability as may be dictated by difficult situations, such as when the patient is far from medical facilities, such as in remote areas of the country, in battle field situations or otherwise unable to quickly or conveniently access professional medical attention.

Storage and Carrying Case

FIGS. 28-36 show a preferred outer or carrying case in which the injectors described herein may be carried in a protected manner. FIG. 28 shows that the preferred carrying case 200 has a lower or bottom part 201 and an upper or top part 202. The upper and lower parts are joined by a detachable 210 joint used to keep the parts together until such time as an injector, such as injector 30, is needed and can be removed from the carrying case. Before explaining the operation of the carrying case 200, a detailed explanation of the features thereof will now be given.

Carrying case 200 is designed to carry an injector 30 with the driver and trigger end of the injector inserted into the upper case part 202. The muzzle and needle end of the injector is inserted into the lower case part 201.

In the preferred construction shown, a bottom end receptacle 205 receives the muzzle end of the injector. This is preferably done so that the sheath remover 80 front wall 82 bears upon a support ledge 206. Ledge 206 is preferably padded with an annular pad 209. This construction prevents loading of the exposed needle sheath 19 to forces that develop during movement, handling and mishandling (such as dropping) of the carrying case with injector supported therein.

The length between ledge 206 and the upper end of the case top piece 202 is nearly equal in length to, but slightly shorter than the length of, the injector between the safety cap 56 or other top end piece and the face surface 82 of the sheath remover 80. This construction advantageously provides a small amount of clearance so that the injector 30 is not loaded (compressed) in an axial manner when stored in the carrying case.

FIG. 28 shows that the upper part 202 of the carrying case 200 is advantageously provided with a clip mount 206 which can be welded to the upper part 202 or integrally formed therewith during molding of the upper part 202. The clip mount 206 is used to mount a clip 207 which is similar to a clip on a pen. The clip 207 is preferably made of metal having spring properties that hold the clip end 208 against the upper case piece 201. The clip 207 may be used to help hold the carrying case in a user's pocket or in luggage, brief cases, cosmetic bags or in or on other parts of a user's garments or accouterments.

FIGS. 34 and 35 show the clip mount 206 in greater detail. Other configurations are also possible. In any design the mount is preferably durable and prevents the clip 207 or mount 206 from being broken from the carrying case upper part 202.

FIG. 28 shows that the upper and lower case parts 202, 201 are preferably constructed so as to form a detachable joint 210. Although a threaded joint is acceptable, it has been found more preferable to have a joint which can be easily and quickly disconnected so that in an emergency the injector can be accessed quickly to administer a medicine without delay. In the construction shown, the bottom part 201 includes an insertion part 220 (FIG. 29) which is sized and shaped to fit within an insertion receptacle 230 (FIG. 36) formed on the open complementary end of the upper case part 202. Insertion section 220 is advantageously provided with a retainer projection or projections 221 which are received within an annular recess 231 (FIG. 36) to provide a catch or mating engagement which retains the two case parts together until needed by a user.

The connection joint 210 is also advantageously provided with quick release which can be provided in the form of two projections 241 which are received in complementary receptacles formed on the mating part 201. The projections 241 are preferably semicircular to mate into semicircular receptacles 242 adjacent to the insertion part 220. This configuration allows the case to be easily opened by twisting the two case parts 201 and 202 relative to each other only a relatively small angular displacement. The semicircular projections and receptacles thus interact to cam the two case parts away from one another and dislodge the retainer projections 221 from the annular recess 231. Thus, by merely twisting the two case parts less than about 1/10th of a rotation, the carrying case is opened and the injector contained therein may be easily removed.

FIG. 36 also shows a shoulder 232 which is recessed an amount so that the insertion section 220 extends into the joint receptacle bringing the end surface of the insertion part into engagement with the shoulder 232. This also facilitates proper extension of the insertion part into the receptacle so that the projections 221 properly fit into the annular groove 231.

Kits

The invention includes a kit for administration of epinephrine to a patient in need thereof, such as a patient experiencing anaphylaxis, an anaphylactoid reaction or a set of symptoms resembling anaphylaxis or anaphylactoid reaction of unknown etiology but suspected of being an allergic emergency. The kit includes an injector according to the present invention as well as such additional matter as may be necessary to ease administration of the epinephrine to the patient. In some embodiments of the invention, included in the kit is an injector that provides a first dose and a second dose delivered by automatic injection from the same device. In other embodiments, included in the kit is an injector that provides a first dose and a second dose delivered by manual injection from the same device, and in other embodiments, included in the kit is an injector that provides one dose is administered by manual injection and the other dose by automatic injection, and in particular, the injector provides a first dose delivered by manual injection and a second dose delivered by automatic injection from the same device.

In some embodiments, the kit according to the invention provides includes an injector according to the invention and printed instructions for using the kit. In some embodiments, the printed instructions include one or more directions to perform one or more operations as described above. For example, for a first dose manual injection and a second dose automatic injection, the printed instructions include directions to perform one or more of the following functions: (1) remove the needle safety sheath 19; (2) remove the safety cap 55; (3) apply the nose cap 45 to the thigh or other thick muscular tissue with sufficient force to automatically trigger the release 53, thereby activating the device 30 and injecting the epinephrine solution into the patient; (4) remove the nose cap 45; (5) extract the syringe subassembly 10, 11 from the injector barrel 35; (6) remove the collar; (7) insert the needle 17 into the patient; (8) manually depress the plunger 14, thereby manually injecting epinephrine solution into the patient; (9) withdraw the needle 17 from the patient; (10) replace the needle subassembly 10, 11 into the container 200; and (11) safely dispose of the container 200 containing the spent needle subassembly 10, 11. Other instructions may be included within the scope of the invention. The directions may be written in such a way as to convey necessary information for: self-administration of the first and/or second doses by and to the patient; administration of the first or second dose by someone other than the patient to the patient; and self-administration of either the first or second dose combined with administration of either the first or second dose to the patient by someone other than the patient.

In some embodiments of the invention, the kit according to the invention includes a container 200 according to the invention. The kit is provided with the device 30 within the container 200. The kit provides additional protection for the ampule 12 and hub 21 or 90 within the device 30. Additionally, the kit provides a convenient package for carrying the automatic injector 30. In some embodiments, the container 200 may be moisture resistant or even water proof; and may in some instances be of sufficient buoyancy that the kit will float when properly assembled, thereby providing a suitable and convenient package for transporting the device 30 under extreme conditions, such as kayaking, canoeing and other aquatic sports.

Added Methods and Operation

In addition to the various descriptions given elsewhere herein concerning methods and operation of the inventive components, the following added explanation is provided to supplement the description. Description of the device herein is also applicable to device for a first automatic injection and a second manual injection disclosed in a previous application (Ser. No. 11/175,543).

A method aspect according to the present invention is provided for driving a syringe needle 24 or 17 to a selected penetration depth. Aspects of the method will be discussed along with a description of operation and use of the invention.

The process initially includes placing the injector in a cocked position. This is preferably done during manufacture. The injector is cocked with the safety cap 55 removed and pressing the driver bar 37 rearwardly. The barbs 54 on the driver bar 37 are moving and then extending into hole 60 at the trigger end of firing sleeve 57. This performs a compressing of the drive spring 50 and catching of the barbs 54 upon annular piece 43. Once the device is cocked, the safety cap 55 can be installed to prevent accidental firing of the driver 36. This action places the pin 56 between the barbed legs of the driver bar 37. Pin 56 prevents the barbed ends from moving toward one another and releasing the driver bar 37 or shaft. This readies the apparatus for reception of the selected syringe assembly.

Then the process involves selecting a suitable syringe subassembly 11, which is preferably pre-loaded with epinephrine solution as described herein. The selecting involves syringes having the desired fluid volume, injection needle length and durability for the intended purposes. In preparation for installation of the syringe subassembly 11, the plunger rod 62 may be attached to the syringe plunger 14, which allows for performance of a step in which at least one stop collar 64 is attached to the plunger rod 61 for dosage control, as the syringe is provided with a multiple dose charge, as described herein. If the plunger rod 61 can be adjusted for axial length, then adjusting the plunger rod 61 occurs at this time to provide a desired or consistent discharge volume or dose (0.3 mL or 0.15 mL of epinephrine solution, depending on the target patient size and/or age). Thus a step of determining a dosage to be dispensed from the apparatus is accomplished. Once adjusting and/or determining step has been completed, the dose setting step is complete.

Further preferred methods include inserting a selected syringe subassembly 11 through the open forward end of barrel 31. The methods further include locating and installing the syringe subassembly 11 to a desired position within the interior of barrel 31. This is accomplished with the nose cap 45 removed and by sliding the selected syringe subassembly 11 with the open end 13 first, into the barrel cavity 35.

The above steps and procedures according to the inventions may in general be accomplished with either the fixed needle or double needle syringe subassemblies 10 or 11.

Further processes according to the invention may also include adjusting penetration depth. Adjusting penetration may be accomplished by selecting a desired penetration controller 38, spring penetration controller 38 or other penetration controller 38, having a length which positions the abutment surface 39 at a desired location. This may include a selectable number of penetration stop positions. This can be accomplished while the nose cap 45 is separated from the barrel 31 either by placing a selected length of penetration controller 38 sleeve 38 into the nose cap, or by placing a selected penetration controller 38 spring 75-79 into the nose cap. A combination of control spring and fixed control element may also be possible.

In the example illustrated in FIGS. 3-6, the sleeve type penetration controller 38 is used, and is frictionally positioned within the cap to abut the nose cap interior front wall adjacent the needle aperture 34. Return spring 71 is also placed within sleeve 70, prior to installing the controller and spring subassembly 11 into the nose cap 45 interior cavity. This is preferably done with the enlarged end of the spring engaging the front, flanged end 170 of sleeve 38.

The spring, penetration controller 38 and nose cap assembly 45 can then be installed to the barrel 31. This is advantageously done in the illustrated embodiments by threading the nose cap 45 onto the barrel 31 until the stop shoulder 47 is engaged by the rearward end of the nose cap 45, to assure proper axial spacing between the syringe abutment surface 39 and the syringe hub 21 or 90. The return spring 71 may be made to abut a ring-shaped stainless steel guide and load distributor 171 (FIGS. 24 and 25) to help assure accurate firing and less decelerated stopping of the syringe subassembly 11.

Alternatively, a spring of selected compression length (for example, one of the springs 75-79) can be used to determine penetration depth. In this aspect, a spring is selected that has a compressed axial length related to a desired needle penetration depth. The selected spring is then mounted to the nose cap 45, such as by frictionally sliding the spring into place within the cap and/or along with the guide 171. Now the end of the spring facing the syringe hub becomes the syringe abutment surface and the penetration depth will be gauged by the fully compressed length of the spring. The spring may have various number of active coils and in some designs dead coils to help provide desired penetration with sufficient energy for penetration. Once the selected spring is mounted within the nose cap, the assembly can be threaded onto the barrel 31 to a point where the stop shoulder 47 is engaged.

The sheath remover 80, if not already in position on the nose cap 45, can be slid into position on the nose cap 45, to position the sheath engaging fingers 82 over the sheath 19. The fingers 82 will perform by flexing, thereby allowing the sheath remover 80 to act by sliding over the extent of the needle sheath 19 that is exposed forwardly of the nose cap 45.

Once the nose cap 45 and sheath remover 80 are in place and the safety 55 is attached, the device 30 is loaded, cocked and in a safe condition nearly ready for use. The device 30 can be safely carried or stored in this condition until such time that an injection is to be administered. In some embodiments, the device 30 is placed within the container 200, in the manner described above.

Single or Double Automatic Injections

The following discussion will describe a single automatic dose use, and a double automatic dose use of the illustrated and other auto-injectors according to the invention. The described uses are both possible using the same or similar procedures with a single fixed needle syringe subassembly 10, or the double needle syringe subassembly 11, although the latter is considered to have several advantages, including improved shelf life of the epinephrine solution.

Prior to injection, the user can remove the protective sheath 19 from the syringe subassembly 10 or 11 by moving, such as by sliding, the sheath remover 80 forwardly. This performs a disengaging step, freeing the sheath remover 80 from the nose cap 45. The sheath remover 80 fingers 82 perform by engaging and catching or binding against the sheath lip 89. Further removal of the sheath remover 80 applies axial forces upon the sheath 19 that act by pulling the sheath 19 outwardly through the needle aperture 34 in the nose cap 45. The sheath remover 80 thus performs an action of removing the sheath 19 from the syringe assembly and other parts of the auto-injector.

To perform a single automatic injection (or an automatic first dose injection in the case of double automatic injection), the user may first perform a removing step to remove the safety 55 form the opposite end of the barrel 31. This is advantageously done by pulling the safety 55 and attached safety pin 56 from between the barbed legs 54 of the driver bar 37 or other driver bar assembly. This arming step involves removing or disabling the safety, thus readying the injection device for dose administration.

Next, the user presses the nose cap against the tissue area to be injected. The pressing action causes movement of the firing sleeve 57 forwardly relative to the barrel 31. The barbs 54 on the driver bar 37 or shaft assembly will move toward one another collapsing inwardly by engaging the barbs 54 against the walls of opening 60. This action releases the driver bar 37, which is now allowed to move forwardly, such as by sliding, in response to force applied by the driver spring 50. This forcing of the driver bar 37 serves to free the driver release 53 into a driving action wherein the driver bar 31 moves forward and acts by engaging the plunger rod 61. The driving action also forces the syringe subassembly 10 or 11 forward. This acts by penetrating the adjacent tissue of the patient (who may be the same person as the user, wherein the user is self-administering epinephrine solution, or may be a person other than the user) with the needle 17 (or needle 24 and also the forward movement provide the penetrating force for needle 22 to punch through the seal of the ampule 12).

As the syringe subassembly 10 or 11 moves forwardly, the return spring 71 or selected penetration controller springs 75-79 are acted upon to perform a compressing of the forward spring. The spring 71, nose cap 45 and any penetration controller 38 act by restraining and stopping the forwardly moving needle hub 21 or 90. In arrangements in which the engaged end of the return spring also constitutes the syringe abutment surface, the selected spring will fully compress at a preselected axial location, stopping needle penetration at the desired penetration depth. The same penetration depth can be effected in arrangements in which the return spring 71 compresses to a point where the needle hub engages the fixed abutment surface 39 on the selected sleeve type penetration controller 38. Penetration depth is determined by the selected axial position of the abutment surface, whether it is on a penetration controller 38 sleeve or by fully collapsing a spring having a desired fully compressed length.

Once the abutment surface or full spring compression point is reached, the driver spring 50 will continue pushing the plunger rod forwardly, dispensing epinephrine solution (preferably 0.3 mL or 0.15 mL). In instances where a single needle syringe subassembly 10 is used, continued forward motion of the plunger 14 will result in injection of the epinephrine solution, which is also injected when a double needle syringe subassembly 11 is provided within the barrel 31, but after the ampule 12 is driven forward onto the seal penetrating needle 22.

Epinephrine solution will be injected as the driver spring 50 performs by forcing the 14 plunger forwardly. Such forcing continues until such time that the plunger shaft engagement head 63 engages any desired stop collar 64 or stack of stop collars. This marks the end of the single automatic injection (or the first dose automatic injection in the case of double automatic injections), and the prescribed dosage amount will have been injected at the selected injection penetration depth. FIG. 4 shows an example of the medicine delivery device of this invention after the single automatic injection (or the first does automatic injection in the case of double automatic injections).

Figure 37:
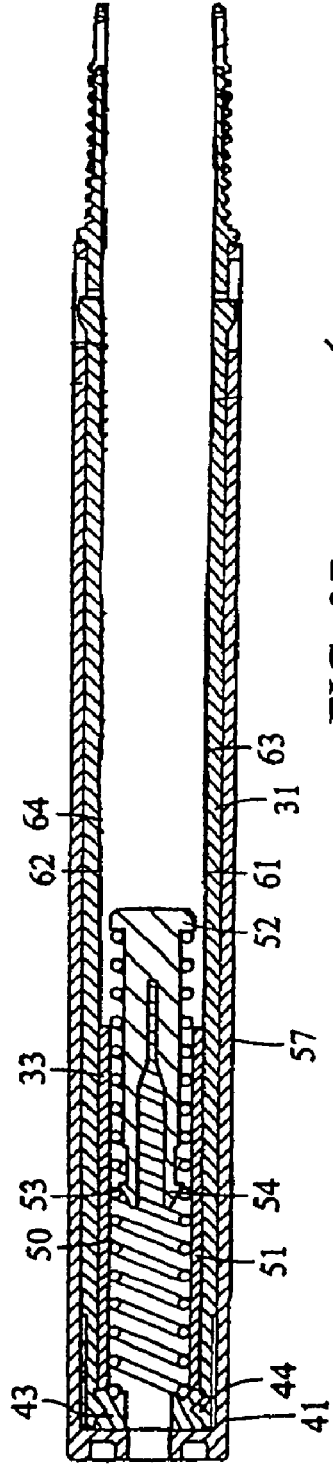
FIG. 37 shows an example of one embodiment of the device of the invention after the removal of the syringe subassembly.

To perform administration of a second dose by automatic injection in the case of double automatic injection, in some embodiments the user first removes the nose cap subassembly (comprising the nose cap 45, return spring 71, and penetration controller 38) and then withdraws the syringe subassembly from the barrel 31 through the barrel's muzzle end. The next step is to remove the stop collar 64. The removable stop collar 64 is designed for halting movement of syringe driver 37 at an extended position after the syringe driver 37 has been released. Stop collar 64 is provided within barrel 31 and positioned at least partially around plunger stem 62 of the syringe subassembly. Stop collar 64 is radially sized to abut against the end of ampule 12 of the syringe subassembly. FIG. 37 shows an example of the device after the removal of the syringe subassembly.

Figure 38:
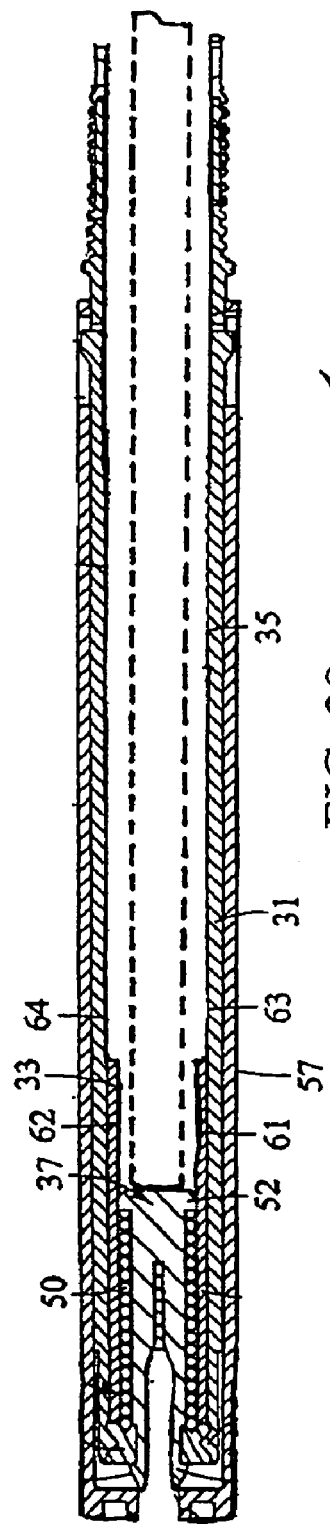
FIG. 38 shows an example to recock the syringe driver 37 for a subsequent injection in one embodiment of the invention. The dotted line illustrates a rod-shaped object such as a pen, pencil, or screwdriver.
Figure 39:
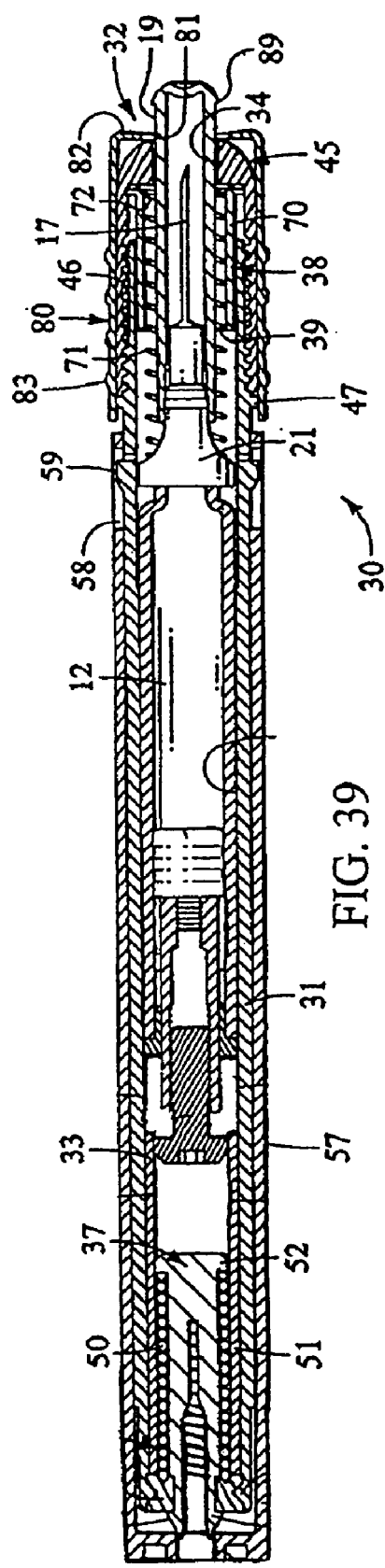
FIG. 39 shows an example of one embodiment of the device of the invention ready for a subsequent automatic injection such as a second automatic injection.
Figure 40:
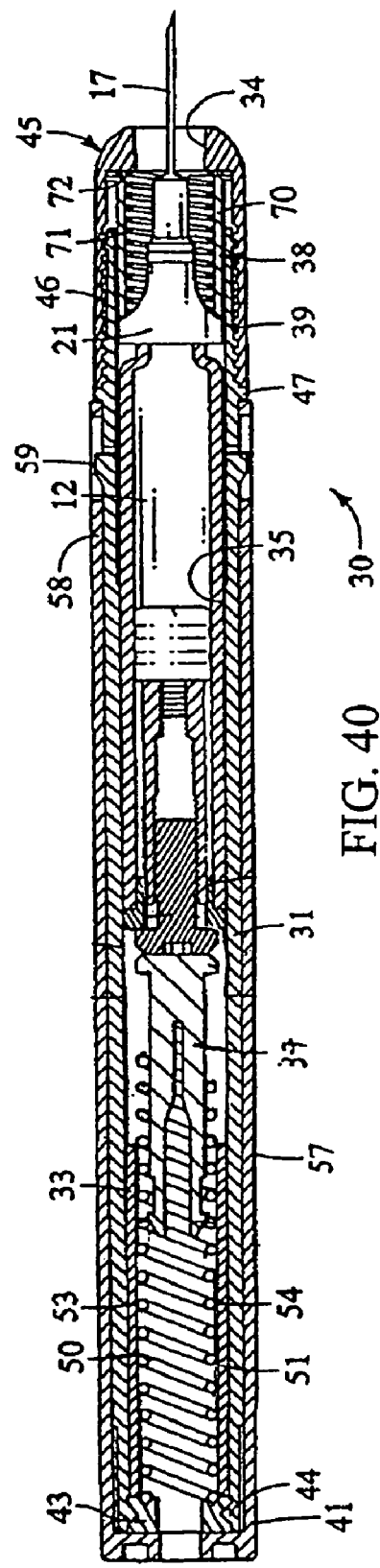
FIG. 40 shows an example of one embodiment of the device of the invention after a subsequent automatic injection such as a second automatic injection.

Stop collar 64 has a predetermined length to provide approximately equal dosages for each injection with the same syringe subassembly. The removal of stop collar 64 enables the plunger stem to move further forward for a subsequent injection. A preferred stop collar is shown in FIGS. 16 and 17, but the stop collar can also be a split design as disclosed in U.S. Pat. Nos. 5,358,489, 5,540,664, and 5,665,071, herein incorporated by references for their entireties. The syringe driver 37 may then be recocked by inserting a thin instrument (such as a rod, pen, pencil, or a screw driver; an example shown as dotted line in FIG. 38) down the barrel 31 and pushing syringe driver 37 against the force of driver spring 50 until the barbed tips 54 constrict and pass through aperture and then spread to lock behind fire bushing 43 (FIG. 38). Safety cap 55 with projecting pin 56 can be optionally reinserted at this point to prevent undesired firing. The syringe subassembly can then be reinserted into the barrel 31 and the nose cap subassembly is reattached. The device is now ready for a second automatic injection. FIG. 39 shows an example of the device ready for a subsequent automatic injection such as a second automatic injection. In preparation for the automatic second dose, stop collar 64 is no longer inside barrel 31 and the device is recocked for a second dose automatic injection. A second dose automatic injection is triggered in the same manner as the first dose automatic injection. FIG. 40 shows an example of the device after a subsequent automatic injection such as a second automatic injection.

The penetration depth and the dosage amount are controllable as discussed above. Penetration depth can be controlled by selecting the axial position at which the needle hub is stopped within the barrel 31 as a function of the selected or adjusted penetration controller 38, such as by penetration controller 38 or the collapsed condition of a penetration controller spring. FIGS. 9 and 10 show an example of penetration depth determined by penetration controller 38 (before and after an automatic injection, respectively), which is designed to stop the movement of the needle hub of the syringe subassembly at a desired position, such as a penetration depth suitable for a subcutaneous injection. If a different penetration depth is desired, penetration controller 38 may be varied in length during manufacturing of the device, for example, to a shorter length which more conveniently enables intramuscular injection in the patient. FIGS. 41 and 42 show an example of a different penetration depth, after, for example without penetration controller 38 (shown before and after an automatic injection, respectively) as compared to FIGS. 9 and 10, which show a penetration depth with penetration controller 38 present.

Double Manual Injections

In the case of double manual injections in one end of the invention, the syringe subassembly 10 or 11 is removed from the barrel 31 by disconnecting the nose cap subassembly followed by the withdrawal of the syringe subassembly through the barrel's muzzle end. The user (patient or someone other than the patient) then manually inserts the forward needle into the flesh of the patient and depresses the plunger rod, preferably with the thumb. For the first dose manual injection, stop collar 64 is employed to stop the plunger assembly of the syringe subassembly for injecting the desired amount of drug. Stop collar 64 is then removed from the syringe subassembly to allow the plunger's further movement for a second dose manual injection. A preferred stop collar is shown in FIGS. 16 and 17, but the stop collar can also be a split design as disclosed in U.S. Pat. Nos. 5,358,489, 5,540,664, and 5,665,071 (which are each incorporated by reference herein in their entirety) or easy removal. The penetration depth of manual injections may even be controlled by the user, and the user may choose to inject an epinephrine solution subcutaneously or intramuscularly.

First Manual Injection and Second Automatic Injection

The following discussion will describe a first dose manual injection, and a second dose automatic injection according to the invention. The described uses are both possible using the same or similar procedures with a single fixed needle syringe subassembly 10, or the double needle syringe subassembly 11, although the latter is considered to have several advantages, including improved shelf life of the epinephrine solution.

To perform the first dose manual injection, the syringe subassembly 10 or 11 is removed from the barrel 31 by disconnecting the nose cap subassembly followed by the withdrawal of the syringe subassembly through the barrel's muzzle end. The user (patient or someone other than the patient) then manually inserts the forward needle into the flesh of the patient and depresses the plunger rod, preferably with the thumb. For the first dose manual injection, stop collar 64 is employed to stop the plunger assembly of the syringe subassembly for injecting the desired amount of drug. Stop collar 64 has a predetermined length to provide approximately equal dosages for each injection with the same syringe subassembly. The removal of stop collar 64 enables the plunger stem to move further forward for a subsequent injection. Stop collar 64 is then removed from the syringe subassembly to allow the plunger's further movement for a second dose automatic injection. A preferred stop collar is shown in FIGS. 16 and 17, but the stop collar can also be a split design as disclosed in U.S. Pat. Nos. 5,358,489, 5,540,664, and 5,665,071 for easy removal. The penetration depth of manual injections is controlled by the user, and the user may choose to inject an epinephrine solution subcutaneously or intramuscularly.

To perform the second dose automatic injection, the syringe subassembly is reinserted into the barrel 31 and the nose cap subassembly is reattached. Please note that syringe driver 37 is still in its cocked position. The user can then remove the protective sheath 19 from the syringe subassembly 10 or 11 by moving, such as by sliding, the sheath remover 80 forwardly. This performs a disengaging step, freeing the sheath remover 80 from the nose cap 45. The sheath remover 80 fingers 82 perform by engaging and catching or binding against the sheath lip 89. Further removal of the sheath remover 80 applies axial forces upon the sheath 19 that act by pulling the sheath 19 outwardly through the needle aperture 34 in the nose cap 45. The sheath remover 80 thus performs an action of removing the sheath 19 from the syringe assembly and other parts of the auto-injector.

Next, the user removes the safety 55 form the opposite end of the barrel 31. This is advantageously done by pulling the safety 55 and attached safety pin 56 from between the barbed legs 54 of the driver bar 37 or other driver bar assembly. This arming step involves removing or disabling the safety, thus readying the injection device for dose administration.

Next, the user presses the nose cap against the tissue area to be injected. The pressing action causes movement of the firing sleeve 57 forwardly relative to the barrel 31. The barbs 54 on the driver bar 37 or shaft assembly will move toward one another collapsing inwardly by engaging the barbs 54 against the walls of opening 60. This action releases the driver bar 37, which is now allowed to move forwardly, such as by sliding, in response to force applied by the driver spring 50. This forcing of the driver bar 37 serves to free the driver release 53 into a driving action wherein the driver bar 37 moves forward and acts by engaging the plunger rod 61. The driving action also forces the syringe subassembly 10 or 11 forward. This acts by penetrating the adjacent tissue of the patient (who may be the same person as the user, wherein the user is self-administering epinephrine solution, or may be a person other than the user) with the needle 17 (or needle 24 and also the forward movement provide the penetrating force for needle 22 to punch through the seal of the ampule 12).

As the syringe subassembly 10 or 11 moves forwardly, the return spring 71 or selected penetration controller springs 75-79 are acted upon to perform a compressing of the forward spring. The spring 71, nose cap 45 and any penetration controller 38 act by restraining and stopping the forwardly moving needle hub 21 or 90. In arrangements in which the engaged end of the return spring also constitutes the syringe abutment surface, the selected spring will fully compress at a preselected axial location, stopping needle penetration at the desired penetration depth. The same penetration depth can be affected in arrangements in which the return spring 71 compresses to a point where the needle hub engages the fixed abutment surface 39 on the selected sleeve type penetration controller 38. Penetration depth is determined by the selected axial position of the abutment surface, whether it is on a penetration controller 38 sleeve or by fully collapsing a spring having a desired fully compressed length.

Once the abutment surface or full spring compression point is reached, the driver spring 50 will continue pushing the plunger rod forwardly, dispensing epinephrine solution. In instances where a single needle syringe subassembly 10 is used, continued forward motion of the plunger 14 will result in injection of the epinephrine solution, which is also injected when a double needle syringe subassembly 11 is provided within the barrel 31, but after the ampule 12 is driven forward onto the seal penetrating needle 22.

Epinephrine solution will be injected as the driver spring 50 performs by forcing the 14 plunger forwardly. Such forcing continues until such time that the plunger shaft engagement head 63 engages any predetermined stop position for the second dose administration. This marks the end of the second dose automatic injection.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

I claim:

1. A drug delivery device containing an epinephrine solution, wherein the device comprises:
    a tubular barrel having a muzzle end with a needle receiving aperture;
    a syringe subassembly receiving cavity situated along the barrel adjacent the muzzle end, adapted to releasably and slidably receive a syringe subassembly for movement toward and away from the muzzle end with a needle of the syringe subassembly being capable of projection through the needle receiving aperture;
    a syringe subassembly held within the syringe subassembly receiving cavity and movable therein;
    a syringe driver connected to the barrel, and having a driver bar movable toward the muzzle end against the syringe subassembly and into the syringe subassembly receiving cavity to move the syringe subassembly for administration of medicine therefrom;
    a penetration controller mounted at the muzzle end of the barrel and having a syringe subassembly abutment spaced from the muzzle end to achieve a desired needle penetration depth position; said penetration controller including a front spring that maintains the syringe subassembly in retracted position within the tubular barrel such that the needle of the syringe subassembly is within the barrel unless the syringe driver is activated to extend the needle of the syringe subassembly projecting it through the needle receiving aperture;
    a detachable nose cap at the muzzle end of the barrel, which allows a user to gain access to the syringe subassembly for administration of a second or subsequent dose if needed by a user, wherein said detachable nose cap and penetration controller with front spring are connected to form a cap and penetration control assembly, which can be removed by release of the detachable nose cap;
    the penetration controller having at least one control sleeve connected with the nose cap and having at least said front spring therebetween;
    a first dose of about 0.3 mL or about 0.15 mL of the epinephrine solution that is injectable by automatic injection and a second dose of about 0.3 mL or about 0.15 mL of the epinephrine solution that is injectable by manual injection, wherein the total amount of the epinephrine delivered between the first and second doses is 0.3 mg or 0.6 mg.

2. The drug delivery device of claim 1, wherein the concentration of the first dose is about 0.5 mg of epinephrine per mL of epinephrine solution or about 1.0 mg of epinephrine per mL of epinephrine solution and the concentration of the second dose is about 0.5 mg epinephrine per mL of epinephrine solution or about 1.0 mg of epinephrine per mL of epinephrine solution.

3. The drug delivery device of claim 1, wherein the device comprises a first dose of about 0.3 mL of the epinephrine solution by automatic injection and means for delivering a second dose of about 0.3 mL of the epinephrine solution by manual injection.

4. The drug delivery device of claim 1, wherein the device comprises a first dose of about 0.15 mL of the epinephrine solution by automatic injection and means for delivering a second dose of about 0.15 mL of the epinephrine solution by manual injection.

5. A drug delivery device containing an epinephrine solution, wherein the device comprises:
    a tubular barrel having a muzzle end with a needle receiving aperture;
    a syringe subassembly receiving cavity situated along the barrel adjacent the muzzle end, adapted to releasably and slidably receive a syringe subassembly for movement toward and away from the muzzle end with a needle of the syringe subassembly being capable of projection through the needle receiving aperture;
    a syringe subassembly held within the syringe subassembly receiving cavity and movable therein;
    a syringe driver connected to the barrel, and having a driver bar movable toward the muzzle end against the syringe subassembly and into the syringe subassembly receiving cavity to move the syringe subassembly for administration of medicine therefrom;
    a penetration controller mounted at the muzzle end of the barrel and having a syringe subassembly abutment spaced from the muzzle end to achieve a desired needle penetration depth position; said penetration controller including a front spring that maintains the syringe subassembly in retracted position within the tubular barrel such that the needle of the syringe subassembly is within the barrel unless the syringe driver is activated to extend the needle of the syringe subassembly projecting it through the needle receiving aperture;
    a detachable nose cap at the muzzle end of the barrel, which allows a user to gain access to the syringe subassembly for administration of a second or subsequent dose if needed by a user, wherein said detachable nose cap and penetration controller with front spring are connected to form a cap and penetration control assembly, which can be removed by release of the detachable nose cap;
    the penetration controller having a control sleeve with features to help maintain connection therebetween, the features selected from the group consisting of, the control sleeve connected to the nose cap with at least portions of the front spring therebetween, the control sleeve having a flange with at least one lobe which engages with features of the nose cap, the control sleeve having a flange with lobes which engage with thread features of the nose cap, the control sleeve having a flange and a spring with at least one enlarged end winding that is positioned between the flange and the nose cap, the control sleeve having at least one lobe that engages in the nose cap;

a first dose of about 0.3 mL or about 0.15 mL of the epinephrine solution that is injectable by automatic injection and a second dose of about 0.3 mL or about 0.15 mL of the epinephrine solution that is injectable by manual injection, wherein the total amount of the epinephrine delivered between the first and second doses is 0.3 mg or 0.6 mg.

6. The drug delivery device of claim 5, wherein the concentration of the first dose is about 0.5 mg of epinephrine per mL of epinephrine solution or about 1.0 mg of epinephrine per mL of epinephrine solution and the concentration of the second dose is about 0.5 mg epinephrine per mL of epinephrine solution or about 1.0 mg of epinephrine per mL of epinephrine solution.

7. The drug delivery device of claim 5, wherein the device comprises a first dose of about 0.3 mL of the epinephrine solution by automatic injection and means for delivering a second dose of about 0.3 mL of the epinephrine solution by manual injection.

8. The drug delivery device of claim 5, wherein the device comprises a first dose of about 0.15 mL of the epinephrine solution by automatic injection and means for delivering a second dose of about 0.15 mL of the epinephrine solution by manual injection.

9. A drug delivery device containing an epinephrine solution, wherein the device comprises:

a tubular barrel having a muzzle end with a needle receiving aperture;

a syringe subassembly receiving cavity situated along the barrel adjacent the muzzle end, adapted to releasably and slidably receive a syringe subassembly for movement toward and away from the muzzle end with a needle of the syringe subassembly being capable of projection through the needle receiving aperture;

a syringe subassembly held within the syringe subassembly receiving cavity and movable therein;

a syringe driver connected to the barrel, and having a driver bar movable toward the muzzle end against the syringe subassembly and into the syringe subassembly receiving cavity to move the syringe subassembly for administration of medicine therefrom;

a penetration controller mounted at the muzzle end of the barrel and having a syringe subassembly abutment spaced from the muzzle end to achieve a desired needle penetration depth position; said penetration controller including a front spring that maintains the syringe subassembly in retracted position within the tubular barrel such that the needle of the syringe subassembly is within the barrel unless the syringe driver is activated to extend the needle of the syringe subassembly projecting it through the needle receiving aperture;

a detachable nose cap at the muzzle end of the barrel, which allows a user to gain access to the syringe subassembly for administration of a second or subsequent dose if needed by a user, wherein said detachable nose cap and penetration controller with front spring are connected to form a cap and penetration control assembly, which can be removed by release of the detachable nose cap;

the penetration controller having a control sleeve with at least one flange which engage with features of the nose cap to help maintain connection therebetween;

a first dose of about 0.3 mL or about 0.15 mL of the epinephrine solution that is injectable by automatic injection and a second dose of about 0.3 mL or about 0.15 mL of the epinephrine solution that is injectable by manual injection, wherein the total amount of the epinephrine delivered between the first and second doses is 0.3 mg or 0.6 mg.

10. The drug delivery device of claim 9, wherein the concentration of the first dose is about 0.5 mg of epinephrine per mL of epinephrine solution or about 1.0 mg of epinephrine per mL of epinephrine solution and the concentration of the second dose is about 0.5 mg epinephrine per mL of epinephrine solution or about 1.0 mg of epinephrine per mL of epinephrine solution.

11. The drug delivery device of claim 9, wherein the device comprises a first dose of about 0.3 mL of the epinephrine solution by automatic injection and means for delivering a second dose of about 0.3 mL of the epinephrine solution by manual injection.

12. The drug delivery device of claim 9, wherein the device comprises a first dose of about 0.15 mL of the epinephrine solution by automatic injection and means for delivering a second dose of about 0.15 mL of the epinephrine solution by manual injection.

* * * * *